(12) United States Patent
Gumennik et al.

(10) Patent No.: US 12,102,734 B2
(45) Date of Patent: Oct. 1, 2024

(54) METHODS FOR CREATING THREE-DIMENSIONAL BIOSYNTHETIC TISSUE

(71) Applicant: THE TRUSTEES OF INDIANA UNIVERSITY, Indianapolis, IN (US)

(72) Inventors: Alexander Gumennik, Bloomington, IN (US); Louis Alexandre van der Elst, Bloomington, IN (US); Merve Gokce Kurtoglu, Bloomington, IN (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 832 days.

(21) Appl. No.: 17/239,322

(22) Filed: Apr. 23, 2021

(65) Prior Publication Data

US 2021/0330864 A1 Oct. 28, 2021

Related U.S. Application Data

(60) Provisional application No. 63/014,206, filed on Apr. 23, 2020.

(51) Int. Cl.
| *A61L 27/00* | (2006.01) |
| *A61L 27/04* | (2006.01) |
| *A61L 27/36* | (2006.01) |
| *A61L 27/38* | (2006.01) |
| *A61L 27/50* | (2006.01) |
| *B33Y 80/00* | (2015.01) |
| *A61L 27/14* | (2006.01) |

(52) U.S. Cl.
CPC .......... *A61L 27/3839* (2013.01); *A61L 27/04* (2013.01); *A61L 27/3633* (2013.01); *A61L 27/50* (2013.01); *B33Y 80/00* (2014.12); *A61L 27/14* (2013.01); *A61L 2300/414* (2013.01); *A61L 2420/04* (2013.01); *A61L 2420/08* (2013.01)

(58) Field of Classification Search
CPC .. A61L 27/14; A61L 27/3839; A61L 2420/04; B33Y 80/00
See application file for complete search history.

(56) References Cited

U.S. PATENT DOCUMENTS

2018/0243478 A1* 8/2018 Pang .................... B33Y 10/00

* cited by examiner

*Primary Examiner* — Jacqueline Woznicki
(74) *Attorney, Agent, or Firm* — Barnes & Thornburg LLP

(57) ABSTRACT

A method of producing bioengineered tissue includes coating a microstructured fiber with a bioink containing a plurality of living cells. The microstructured fiber is embedded with microfluidic channels defining periodic outlet apertures, a plurality of ultrasonic transducers, at least one chemical sensor, and at least one temperature sensor. The method further includes applying the coated fiber to an anatomic model of an organ. The microfluidic channels and outlet apertures of the fiber are configured to function as an artificial blood-vessel system to the bioengineered tissue, thereby supplying building material for the proliferation of the plurality of living cells, and allowing the bioengineered tissue to mature into functional tissue.

20 Claims, 12 Drawing Sheets

- WIRES CONTACTING ULTRASONIC TRANSDUCERS
- MICROFLUIDIC CHANNELS WITH OUTLETS
- HUMAN UMBILICAL VEIN ENDOTHELIAL CELLS (HUVEC) FORMING BLOOD VESSELS
- TISSUE CULTURE CELLS IMMERSED IN BIOINK
- ULTRASONIC SIGNAL FOR CELL-SENSING
- FIBER CLADDING
- VASCULAR ENDOTHELIAL GROWTH FACTOR (VEGF)

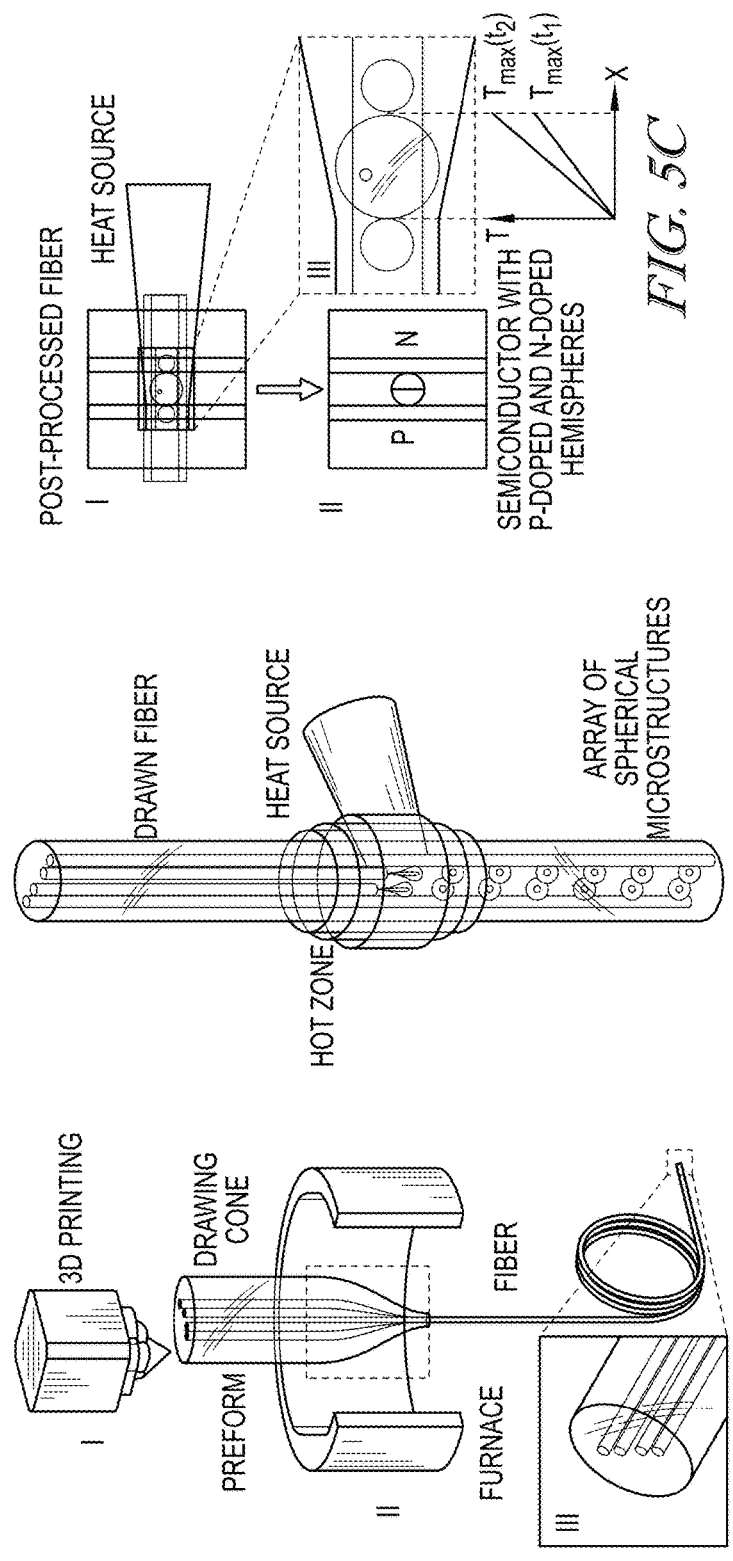
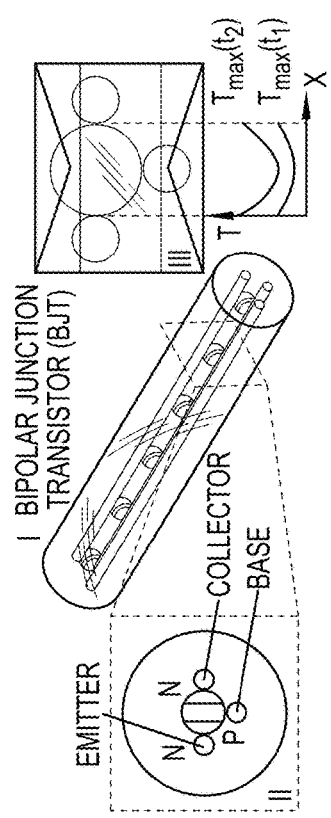
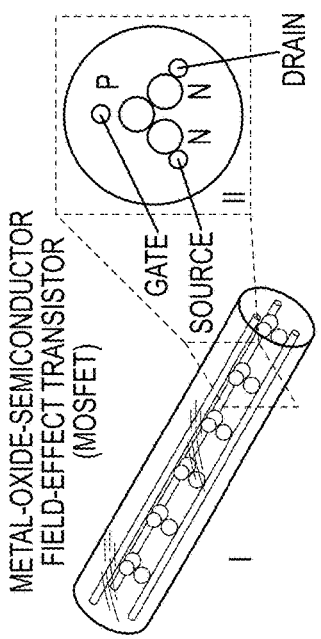
FIG. 5A  FIG. 5B  FIG. 5C  FIG. 5D  FIG. 5E

METHODS FOR CREATING THREE-DIMENSIONAL BIOSYNTHETIC TISSUE

CROSS-REFERENCE TO RELATED APPLICATIONS

This application claims priority to U.S. Provisional Application Ser. No. 63/014,206, filed on Apr. 23, 2020, the contents of which are incorporated herein by reference.

Cross-reference is made to U.S. application Ser. No. 17/238,833, filed Apr. 23, 2021, titled "A GUT BIOREACTOR AND METHODS FOR MAKING THE SAME" and identified. Cross-reference is made to U.S. application Ser. No. 17/239,100, filed Apr. 23, 2021, titled "VERY LARGE SCALE INTEGRATION FOR FIBERS (VLSI-Fi)" and identified. The contents of each of these applications are incorporated herein by reference in their entireties. Neither of these cross-referenced applications is admitted to be prior art with respect to present application by its mention in the cross-reference section.

BACKGROUND

Realistic bioengineered tissues and organs may have broad medical and societal benefits. Complex wound infilling, limb and organ regeneration and prostheses, and correction of inborn defects in humans or other animals are perennial medical needs that can be addressed by bioengineered tissues and organs. Despite decades of progress in bioprinting, however, the control over tissue microstructure that is essential to healthy tissues and organs remains a challenge that impedes development of artificial tissues and organs suitable for transplantation. One of the key issues limiting the construction of engineered tissues for use in human medicine is that tissues in the body receive constant supplies of oxygen and nutrients, and eliminate waste, through the flow of blood and lymph through a dense network of microvasculature that penetrates everywhere in the tissue, whereas known engineered tissues are avascular and must obtain oxygen and nutrients and eliminate waste through their surfaces. Moreover, in a real tissue, no cell is more than a few tens of microns from a blood vessel, whereas in known engineered tissue a cell may be many millimeters away from a supply source in an engineered tissue. Surface exchange of oxygen is and nutrients in known engineered tissue is much less efficient than vascular supply and also lacks the signals essential for tissue maturation and maintenance than can be sent by blood flow in vessels of a real tissue.

A result of these differences is that while cells may be laid down in complex patterns in an engineered tissue, many of these cells die or malfunction long before the putative tissue is implanted in the target organism. A variety of approaches to providing better volumetric supply of oxygen and nutrients to tissues has not proved very successful. The majority of them rely on diffusion, thus the thickness of tissues receiving a satisfactory supply of nutrients and oxygen is limited to a diffusion length, of the order of a hundred microns. This limits printed tissues to a thin-layer configuration. In addition, normal tissue development and homeostasis depend on the formation of extracellular matrix with specific and complex fiber architectures and on local and long-range signaling, which lead to adaptive remodeling and self-regulation of tissues. These factors are largely absent from tissue built using contemporary organ printing. Thus, the way tissues change in the period from construction to implantation, which may require 3-4 weeks of culture before the tissues lay down enough extracellular matrix and build enough cell-cell junctions to be implantable, is often maladaptive.

In infrequent cases where tissues self-organize correctly using known technologies, it is often chance, as local conditions generally have not been measured in real time, and the local factors that are critical to proper tissue maturation have been unknown. That is, 3D in-vivo monitoring of metabolic processes with high spatiotemporal resolution is a problem with no satisfactory solution to date. While techniques that would allow such monitoring; e.g., real-time tomographic imaging, are developing, their performance is still limited. Moreover, even when local tissue conditions are known in real time, methods for changing the local conditions in real time have not been known. Thus, a need exists for systems and methods for engineering tissues and organs that a provide a tissue scaffold, enable monitoring of local tissue conditions in real time, and enable manipulation of local conditions to ensure that the maturing engineered tissue develops and maintains the correct cell types, viability, and appropriate extracellular structures.

It also would be desirable to develop systems and methods for efficient and accurate assessment of drug and chemical toxicity in engineered human tissue without requiring the sacrifice of animals, which may not accurately reflect human pathogenesis. It further would be desirable to create realistic stand-alone tumor models through which development and reaction to treatment is reliably monitored, providing a robust platform for cancer research. Still further it would be desirable to create new medical approaches for trauma treatment, tissue replacement and treatment of diseases of degeneration of aging via the use of functional engineered tissue and organs. Example societal benefits of such developments in engineering functional tissues and organs include improved clinical outcomes for patients who can benefit from receiving bioengineered tissue or from advances in the understanding of pathogenesis, tumor development, and responses to treatment.

SUMMARY

The present disclosure is directed to systems and methods for engineering tissues and organs that a provide a tissue scaffold, enable monitoring of local tissue conditions in real time, and enable manipulation of local conditions to help ensure that the maturing engineered tissue develops and maintains the correct cell types, viability, and appropriate extracellular structures. Such systems and methods advantageously are capable of providing functional tissues and organs for medical applications such as wound infilling, limb and organ regeneration and prostheses, and correction of inborn defects in humans or other animals. Additionally, or alternatively, such systems and methods advantageously may enable efficient and accurate drug-toxicity testing, cancer research, and regenerative medicine. In any such instances, the systems and methods described herein may offer a platform for the design and construction of working three-dimensional tissues or organs, rather than the simple quasi-two dimensional or nearly acellular implants achievable by known means. For example, the systems and methods described herein may provide control over micro-metabolic processes of engineered tissues or organs via 3D monitoring networks of sensors that are usable by external operators of the tissue.

In some embodiments, a system for bioengineering tissue or organs includes a material supply (or "feedstock") for bioprinting in which a microstructured fiber is coated with bioink comprising living cells. The fiber may be embedded with: (1) microfluidic channels containing periodic outlets; (2) an array of ultrasonic transducers; and (3) chemical and temperature sensors. As the coated fiber is laid into an anatomic model of an organ, the microfluidic part of the fiber serves as an artificial blood-vessel system, supplying building material for the proliferation of bioink cells, which will eventually mature into realistic (e.g., functional) tissue. The present disclosure is a methodology for biosynthetic tissue creation that will serve as a platform for investigating and gaining control over micro-metabolic processes, enabling advances in drug-toxicity testing, cancer research, and regenerative medicine. Fiber technology brings to conventional bioprinting and tissue engineering, a new array of biological functionalities such as artificial vasculature, innervation and muscular motion.

Additional embodiments, features, and advantages of the disclosure will be apparent from the following detailed description and through practice of the disclosure. The compounds of the present disclosure can be described as embodiments in any of the following enumerated clauses. It should be understood that any of the embodiments described herein can be used in connection with any other embodiments described herein to the extent that the embodiments do not contradict one another.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 5A-5E are conceptual schematics of a VLSI-Fi technique in accordance with a method of this disclosure.

DETAILED DESCRIPTION

Definitions

Figures 1A, 1B, 1C, 1D:
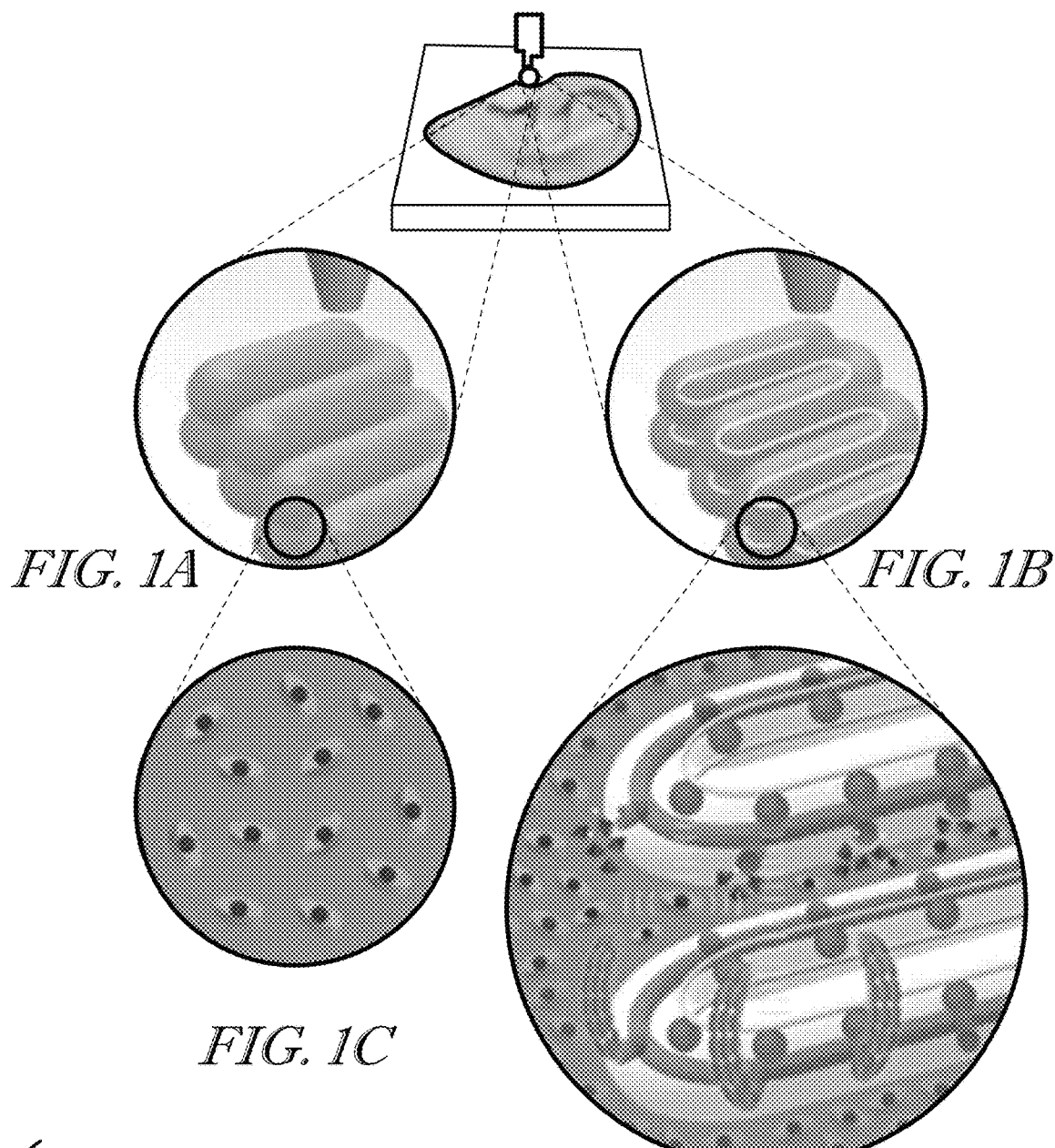
FIGS. 1A-1D illustrate conventional bioprinting in contrast to the inventive bioprinting methods of this disclosure.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

Each of the terms "about" and "approximately," as used herein, mean greater or lesser than the value or range of values stated by 10 percent, but is not intended to designate any value or range of values to only this broader definition. Each value or range of values preceded by the term "about" or the term "approximately" also is intended to encompass the embodiment of the stated absolute value or range of values.

As used herein, the terms "including," "containing," and "comprising" are used in their open, non-limiting sense.

As used herein, the term "engineered" may mean "bioengineered" when used in the context of one or more biological materials.

As used herein, the term "real tissue" may mean tissue produced in vivo by a living, multicellular organism in contrast to "engineered tissue" or "bioengineered tissue."

As used herein, the term "axial patterning" or "axially patterning" means an axial arrangement of discrete devices (e.g., spherical microstructures, or "microspheres") contacted in parallel within a fiber resulting from capillary breakup of initially continuous, separate cores into arrays of the discrete devices As used herein, the term "integrated devices" refers to devices coupled through electronic links, such as common electrical contacts, or photonic links, such as fiber-embedded optical cores.

As used herein, the term "a biological supporting system" or "biological support system" refers to a fiber mimicking natural microstructure of the tissue, including vascular, muscular, and innervation functionalities.

As used herein, the abbreviation "HUVEC" means "human umbilical vein endothelial cell."

As used herein, the abbreviation "VEGF" means "vascular endothelial growth factor."

As used herein, the abbreviation "DEP" means "dielectrophoresis."

As used herein, the abbreviation "ECM" means "extracellular matrix."

As used herein, the abbreviation "FAMES Lab" means "Fibers and Additive Manufacturing Enabled Systems Laboratory."

As used herein, the abbreviation "FOS" means "fiber optic sensors."

As used herein, the abbreviation "FSMA" means "ferromagnetic shape memory alloys."

As used herein, the abbreviation "MRI" means "magnetic resonance imaging."

As used herein, the abbreviation "PZT" means "lead zirconate titanate."

As used herein, the abbreviation "SEBS" means "styreneethylene-butylene-styrene."

As used herein, the abbreviation "SMA" means "shape memory alloy."

As used herein, the abbreviation "VLSI" means "very largescale integration."

As used herein, the abbreviation "VLSI-Fi" means "very large-scale integration for fibers."

A bioengineered system is provided. The bioengineered system comprises a bioink and a fiber. The fiber may extend through the bioink along a first axis. The fiber may comrpise a hollow core and a cladding having an outer surface and surrounding the hollow core. In some embodiments, the cladding is formed to include an outlet that extends from the outer surface to the hollow core so that the hollow core and the bioink are in fluid communication.

In some embodiments, the hollow core has a diameter that is perpendicular to the first axis of about 100 microns to about 300 microns. In some embodiments, the diameter is about 75 microns, about 80 microns, about 85 microns, about 90 microns, about 95 microns, about 100 microns, about 105 microns, about 110 microns, about 115 microns, about 120 microns, about 125 microns, about 130 microns, about 135 microns, about 140 microns, about 145 microns, about 150 microns, about 155 microns, about 160 microns, about 165 microns, about 170 microns, about 175 microns, about 180 microns, about 185 microns, about 190 microns, about 195 microns, about 200 microns, about 205 microns, about 210 microns, about 215 microns, about 220 microns, about 225 microns, about 230 microns, about 235 microns, about 240 microns, about 245 microns, about 250 microns, about 255 microns, about 260 microns, about 265 microns, about 270 microns, about 275 microns, about 280 microns, about 285 microns, about 290 microns, about 295 microns, about 300 microns, about 305 microns, about 310 microns, about 315 microns, about 320 microns, or about 325 microns.

In some embodiments, the outlet has a diameter of about 5 microns to about 25 microns. In some embodiments, the outlet diameter is about 1 micron, about 2 microns, about 3 microns, about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 21 microns, about 22 microns, about 23 microns, about 23 microns, about 24 microns, about 25 microns, about 26 microns, about 27 microns, about 28 microns, about 29 microns, and about 30 microns.

In some embodiments, the hollow core and/or the outlet comprise a core coating. In some embodiments, the hollow core and the outlet each comprise a core coating. In some embodiment, the core coating comprises a first growth factor. In some embodiments, the core coating comprises VEGF.

In some embodiments, the outer surface of the cladding is coated with an outer coating. In some embodiments, the outer coating is a different composition than the core coating. In some embodiments, the outer coating comprises a second growth factor. In some embodiments, the outer coating PDGF.

In some embodiments, the bioink comprises an extracellular matrix and cells distributed throughout the extracellular matrix. In some embodiments, the cells include cardiac cells, neural cells, muscle cells, fetal cells, or vascular cell. In some embodiments, the cells are epithelial cells. In some embodiments, the cells comprise stem cells, engineered cells, induced pluripotent stem cells, or cells related to the vascular system.

In some embodiments, the cladding comprises a biocompatible material. In some embodiments, the cladding comprises plastic, glass, resin, or a combination thereof. In some embodiments, the cladding comprises a polymer. In some embodiments, the cladding comprises polycarbonate. In some embodiments, the biocompatible material is capable of being degraded by the bioink. Degradation may be by hydrolysis or by change in pH.

The bioengineered system may further comprise a sensing fiber. In some embodiments, the sensing fiber includes i) a first metallic core and a second metallic core extending along the axis; ii) a segmented device located between the first metallic core and the second metallic core, and iii) a cladding surrounding the first metallic core, second metallic core, and the segmented device. In some embodiments, the cladding comprises a material selected from the group consisting of COC, PSU, PC, ECOC, SEBS, PDMS, PVDF, PEI, and PMMA.

The segmented device may comprise a first spherical component and a second spherical component. In some embodiments, the first spherical component contacts the first metallic core and the second spherical component. In some embodiments, the second spherical component contacts the first spherical component and the second metallic core.

In some embodiments, the segmented device extends along a second axis about perpendicular to the first axis. In some embodiments, the segmented device is a piezoelectric device.

In some embodiments, the segmented device detects chemicals.

In some embodiments, the segmented device measures a temperature. Illustratively, the measured temperature is the temperature of the environment surrounding the fiber.

In some embodiments, the fiber and the sensing fiber are coupled together.

In some embodiments, the bioengineered system comprises a syringe pump coupled the fiber.

A method of producing a biological support system is provided. In some embodiments, the method comprises bioprinting a bioink and a fiber extending through the bioink along an axis. In some embodiments, the fiber comprises a hollow core and a cladding having an outer surface and surrounding the hollow core. In some embodiments, the cladding is formed to include an outlet that extends from the outer surface to the hollow core so that the hollow core and the bioink are in fluid communication.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination.

The present disclosure is directed to systems including a material supply (or "feedstock") for bioprinting for tissue engineering, in which a microstructured fiber is coated with bioink incorporating living cells. Fiber technology brings a new array of biological functionalities to bioprinting and tissue engineering, such as artificial vasculature, innervation and muscular motion. The inventive systems and methods using fiber technology as described herein may enable building of autologous tissue replacements and eventually entire autologous organs. In one embodiment, the systems described herein may enable growth of engineered replacement liver or muscular tissue from cells sourced from a patient's own body (to avoid rejection issues) within 5-10 years and may enable growth of entire replacement organs (like hearts, livers or pancreas) within 10-15 years.

FIG. 1A illustrates a structure resulting from known (i.e., conventional) bioprinting and FIG. 1C illustrates a microstructure of known bioprinting. Although known bioprinting systems and methods may be capable of shaping cells into anatomic models resembling organs, the known bioprinting systems and methods are too coarse to impart to those models the necessary tissue microstructures, such as blood vessels and nerves that would allow such models to function as organs. Known printed "tissues," on a micro-level, are typically organ-shaped "soups" of cells immersed in a gel matrix. Such known printed tissues lack nutrient and oxygen supplies from inside the printed tissue, which may result in prolonged hypoxia and poor cell survival.

In contrast to known printed "tissues" and as further described below, fibers in accordance with one or more embodiments of the present disclosure are combined with bioink and printed into engineered tissue to provide one or more of: (1) Vasculature—microfluidic channels with periodic outlets for building material and chemicals delivery into the bioprinted volume; (2) Innervation—arrays of ultrasonic transducers to image the tissue density changes and sense instantaneous pressure changes, effectively serving as tactile nerves; and (3) Musculature—shape memory alloys to provide motoric and peristaltic function to the bioprinted system. Additionally, or alternatively, the fibers of the disclosure may be used in one or more of biostimulation and biosensing modalities, shape tracking, peristaltic motion, and bio-chemical delivery to engineered tissue.

In accordance with one embodiment, a microstructured fiber is laid (e.g., printed) into an anatomic model of an organ. The fiber is embedded with microfluidic channels defining periodic outlets and serves as an artificial blood-vessel system, thus configuring the fiber to supply building material for the proliferation of bioink cells and enabling the cells to mature into realistic tissue. For example, the fiber may feed epithelial cells or vascular epithelial growth factors to a desired location, via the microfluidic channels and periodic outlets, to support the natural growth of microvasculature.

FIG. 1B illustrates printing with bioink-coated fiber. In accordance with at least one embodiment, the inventive bioprinting feedstock of the present disclosure provides nutrient and oxygen supplies from inside the engineered tissue via the microfluidic channels and outlets embedded in the fiber, even in newly printed organs that otherwise would be unlikely to survive prolonged hypoxia preceding implantation. For example, the microfluidic channels and outlets provide high-density, continuous flow of a nutrient fluid, allowing the design and construction of true three-dimensional organoids rather than the quasi-two dimensional or nearly acellular implants. As shown in FIGS. 1B and 1D, the tissue resulting from fiber-based bioprinting according to the embodiments described herein will have a rich microstructure, analogous to what would be found in real tissue.

In accordance with one embodiment and as illustrated in FIG. 1D, the fiber is also embedded with an array of ultrasonic transducers and/or sensors. The sensors may be chemical and/or temperature sensors. The ultrasonic transducer array and the sensors embedded into the fiber enable peripheral "innervation," imaging of cell proliferation or death, and monitoring metabolic processes. Innervation of a growing engineered tissue in this manner enables real-time feedback regarding local conditions and spatiotemporal changes within the tissue, which in turn enables regulation of the supply of nutrients, growth factors, and the like to the growing tissue. In this manner, the innervation provided by the ultrasonic transducer array and sensors embedded in the fiber may help achieve healthy tissue with an increased yield.

As shown in FIG. 1D, a fiber of the present disclosure that incorporates micro-channels and ultrasonic cell-density sensors provides an artificial microstructure for engineered tissue and promote the creation of a natural microstructure from within. In this embodiment, the cells are HUVECs are supplied through a fiber in one layer. VEGF or another growth factor may be supplied through a fiber in a consecutive layer. Blood vessels thus grow from the outlets of the first fiber towards the higher concentration of VEGF, i.e. toward the outlets of the fiber in the consecutive layer. By enabling selective addition of a growth factor, the fibers enable localized manipulation of tissue properties. Thus, the fibers solve three problems at once—the creation of a scaffold, the ability to monitor local conditions in real time, and the ability to manipulate local conditions to ensure that the maturing engineered tissue maintains the correct cell types and viability and constructs the appropriate extracellular structures. See FIG. 2.

In accordance with one embodiment, a bioengineering system according to the present disclosure may be applied to artificial gut models. For example, such a bioengineering system may be used to study microbiome complexity in nutrition-related processes. Fibers embedded into a printed gut bioreactor may ultrasonically map buildup of microflora biofilm on the gut walls and may enable monitoring of changes in $CO_2$, pH, and $O_2$ accompanying this process. In such an example, bioinks for the artificial gut models will incorporate intestinal epithelial cells typical in real guts.

In accordance with one embodiment, fibers may be manufactured by a thermal draw of preforms, which is a technique used for fabrication of objects such as optical cables. In the preform, cores of functional and sacrificial materials; e.g., metals, piezoelectrics, semiconductors, and insulators, may be structured to meet the desired electronic and microfluidic functionality of the fiber-embedded devices.

In accordance with one embodiment, the functional cores, flowing out of the thermal draw, may be axially patterned into integrated sensor arrays, and sacrificial cores are patterned and etched out to define the microfluidic system.

In accordance with one embodiment, the axially patterning of the fibers is done through a spatially coherent and material-selective capillary breakup process.

In accordance with one embodiment, the fiber is coated with bioink incorporating living cells.

In accordance with one embodiment, a bioengineering system includes piezoelectric elements configured to measure surrounding cell density by the ultrasonic transducer array to provide a feedback of microenvironmental conditions within the engineered tissue.

In accordance with one embodiment, a bioengineering system includes wires of a shape memory alloy that provide peristaltic motion.

In accordance with one embodiment, a method includes bioprinting using CELLINK's Bio X bioprinter or the like. Such a printer may provide a wide variety of print head technology to enable combination of fibers and bioink and to print a wide variety of materials.

In accordance with one embodiment, a bioengineering system includes gelatin methacrylol (GelMA), which is a biocompatible hydrogel derived from gelatin to which methacrylate and methacrylamide groups were added. GelMA as a bioink provides an excellent extracellular matrix to the cells to create tissue-like structures. The mechanical properties of GelMA, such as printability, elasticity, and stiffness, may be tuned for customization and used in 3D printing.

Figure 3A:
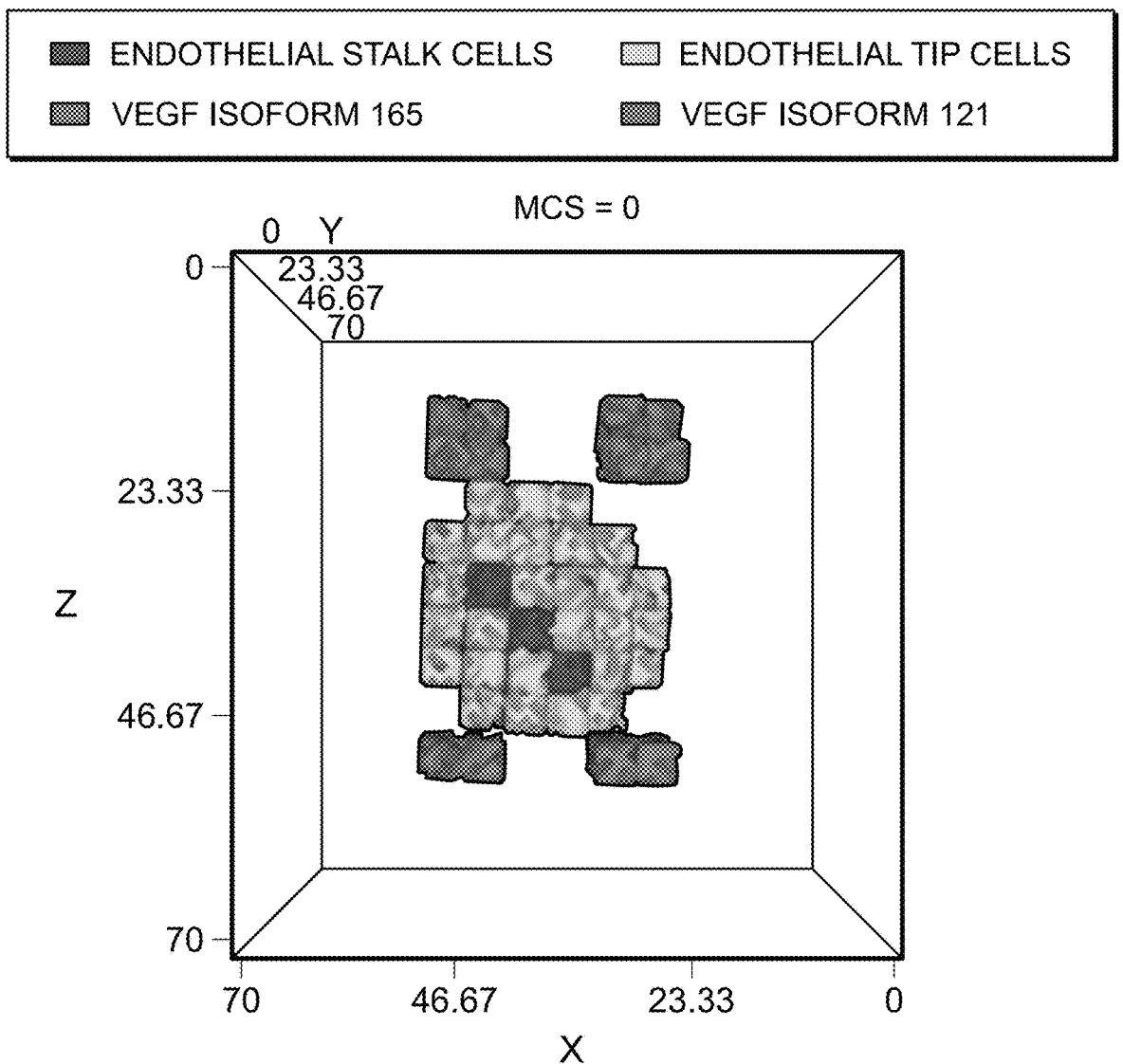
FIGS. 3A-3C illustrate cell behaviors at different Monte Carlo Steps (MCS) representing about 1 minute in accordance with a method of this disclosure.
Figure 3B:
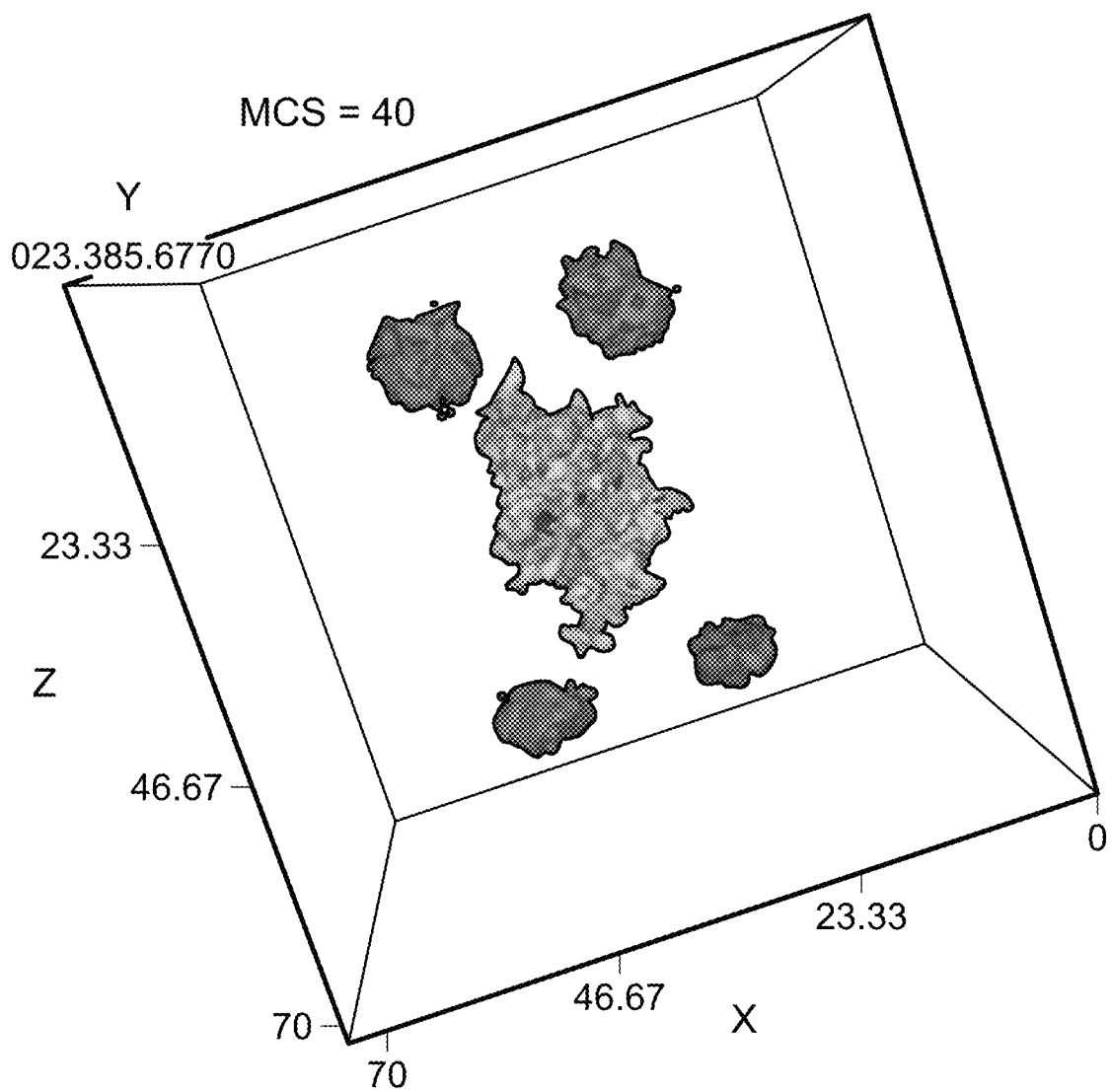
Figure 3C:
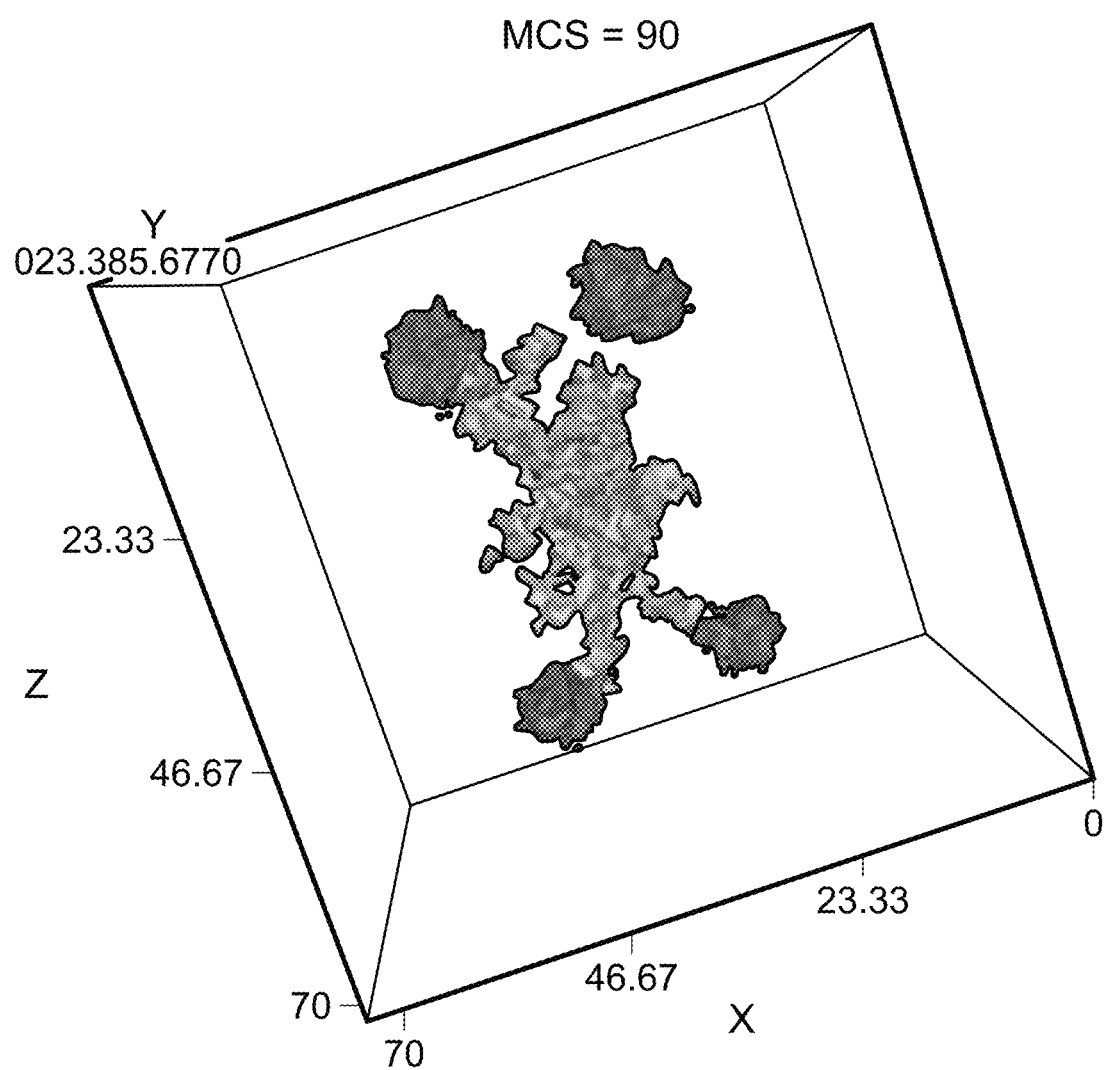
Figure 4A:
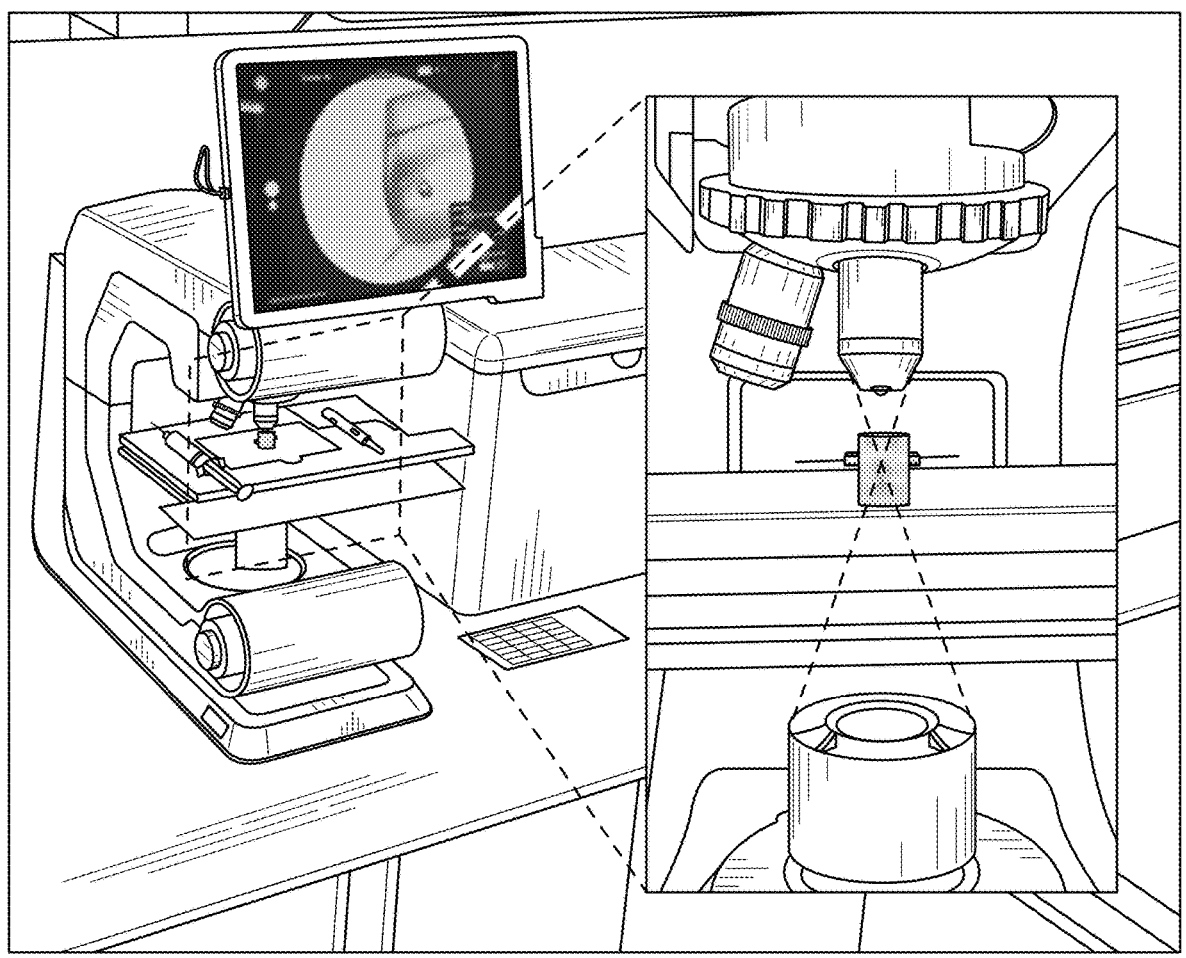
FIGS. 4A-4D illustrate aspects of a TrophoWell device as described herein.
Figure 4B:
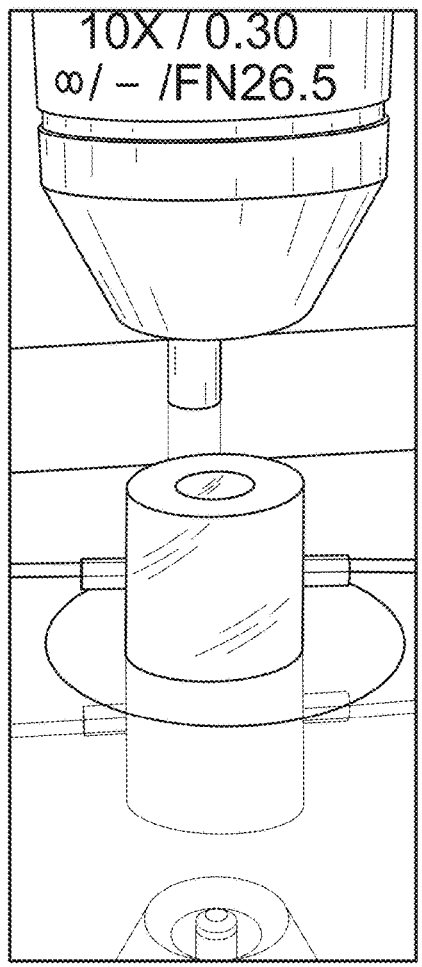
Figure 4C:
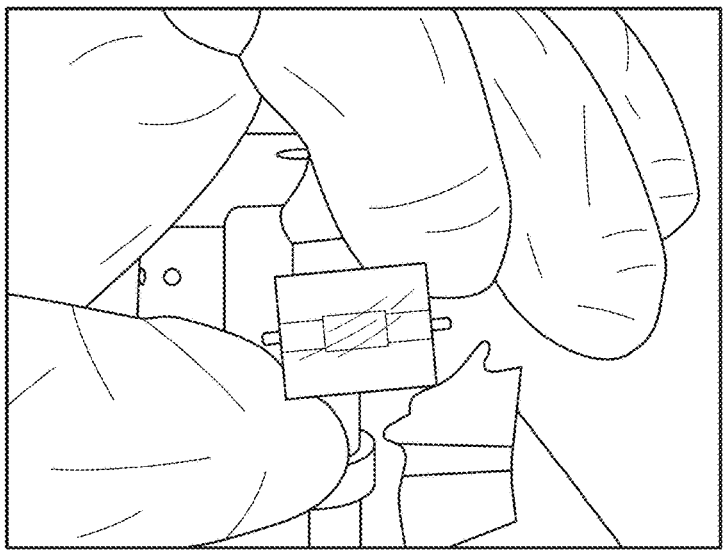
Figure 4D:
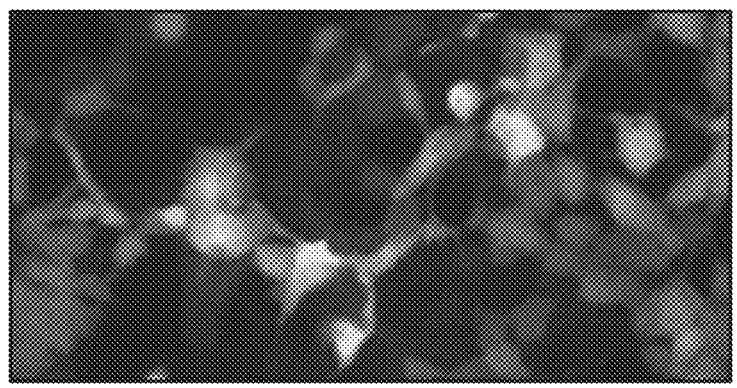

In accordance with one embodiment, vascularization of tissue engineered in accordance with this disclosure may be modeled in 3D using lattice-based tissue modelling platform CompuCell3D. For example, sprouting of new blood vessels by endothelial tip and stalk cells which diffuse in extracellular matrix may be visualized in this manner. The chemotaxis of the cells towards Vascular Endothelial Growth Factors (VEGF) may be simulated using CompuCell3D. An example is illustrated in FIGS. 3A-3C, which illustrate cell behaviors at different Monte Carlo Steps (MCS) representing about 1 minute in accordance with a method of this disclosure.

Figure 6A:
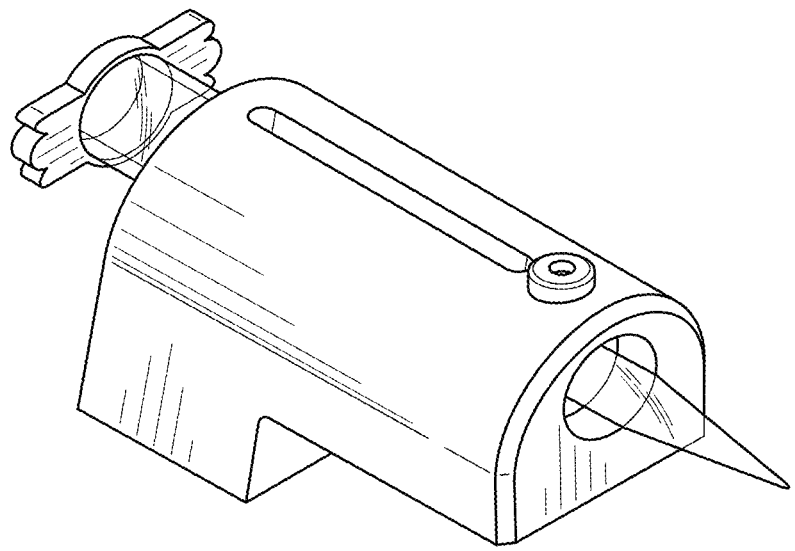
FIG. 6A illustrates a Bio X printhead structure.
Figure 6B:
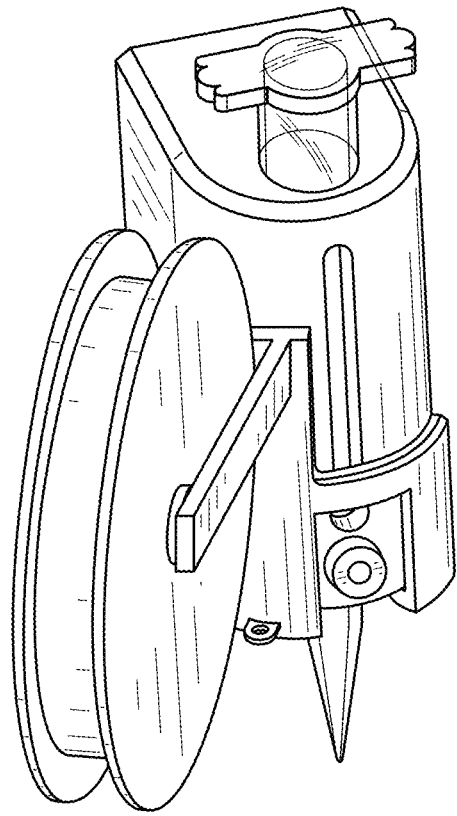
FIG. 6B illustrates a spooling system for fiber alongside the Bio X printhead structure of FIG. 6A.
Figure 6C:
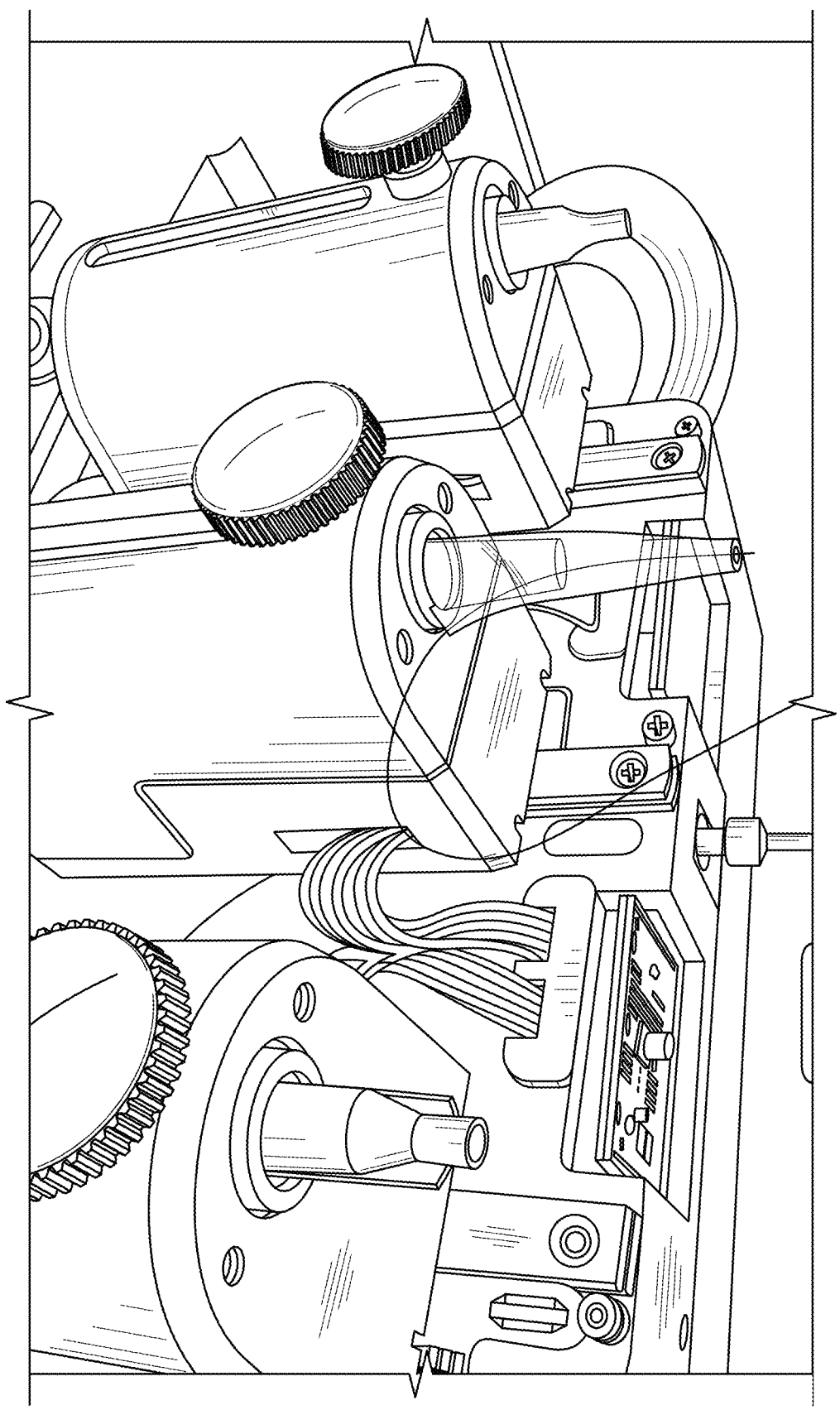
FIG. 6C illustrates an example bioprinting system usable in an embodiment of this disclosure.

In accordance with one embodiment, a tissue platform "TrophoWell" may be used as a testing platform to observe effects of biochemical stimuli on cell development; e.g., in tracking cells such as fluorescent human embryonic kidney cells (HEK 293) under a microscope. The TrophoWell is an upgradable device designed to test biological functions in tissue engineering, such as (1) an early-stage testing resource of drugs, chemicals, or other biological agents that affect the human body; and/or (2) for the testing of biochemical and physical reactions for medical purposes personalized to specific patients. An example is illustrated in FIGS. 4A-4D. More information about the TrophoWell device may be found in U.S. application Ser. No. 16/834,572, the contents of which are incorporated herein by reference in their entirety. Features of an example bioprinting system are illustrated in FIGS. 6A-6C.

Manufactured and Bioprinted Fibers for Use in the Embodiments

Aspects of manufactured and bioprinted fibers that may be used in the embodiments described above now will be presented. Such methods and systems are described in "Towards Digital Manufacturing of Smart Multimedia Fibers" by Faccini de Lima et al., *Nanoscale Research Letters* (2019) 14:209, which is incorporated herein by reference in its entirety.

Functions of the embodiments described herein are enabled by using in-fiber microfluidic channels to deliver cells and signaling biochemicals and shape memory alloy wires for movement control, and piezoelectric elements to map the environment by ultrasound waves. The fibers defining such channels may be thermally drawn from 3D printed multimaterial rods called preforms. Conventional preform fabrication techniques, such as thin-film-rolling and stack-and-raw, are limited in producing complex geometrical structures, take up a significant amount of time in the fiber draw process, and require skilled labor and expensive equipment. 3D printing addresses these problems with the help of soluble support material and its partly automated and user-friendly process, thereby enabling the printing of complex geometries with ease in a relatively short period of time. Thus, it may be advantageous to include fibers thermally drawn from 3D printed preforms in the embodiments described herein. Such 3D printed preforms may be formed from one or more materials such as polycarbonate or glass (e.g., soda-lime glass, silica glass, or bismuth glass). In some examples, the preforms may include at least one fiber selected from the group of materials comprising cyclic olefin copolymer (COC), polysulfone (PSU), poly(methyl methacrylate) (PMMA), polycarbonate (PC), styrene ethylene butylene styrene (SEBS), polyvinylidene fluoride (PVDF), polyetherimide (PEI), ECOC, and polydimethylsiloxane (PDMS).

After the 3D preforms are printed, they may be drawn into fibers and further processed, as illustrated in FIGS. 5A-6C. FIG. 5A shows the 3D-printed preform (I) being thermally drawn into a long, thin fiber. FIG. 6B illustrates a fiber being reliquefied by heating to allow for the breakup of the cores in a spatially coherent material-selective manner, enabling an axial control over the fiber embedded structures. FIG. 5C illustrates segregation-driven control of doping in (1) post-breakup semiconducting particles, allowing (II) control of an individual device's internal architecture via (111) thermal gradient. FIG. 5D is (1) a schematic illustration of metal-oxide-semiconductor field-effect transistor (MOSFET) through VLSI-Fi, where the p-type and n-type semiconductors. FIG. 5E shows a schematic picture of a bipolar junction transistor realized by VLSI-Fi, achieved with impinging heat sources from both the emitter and collector sides.

Method of Producing Channels and Periodic Outlets in the Microstructure Fibers

In an effort to mimic the natural structure and environment of a vascularized system, channels and periodic outlets are produced within the microstructure fibers to, in part, generate a guide for blood vessels and capillaries to form. As exemplified in FIG. 1D and FIG. 9 (part IV), the channels and outlets form scaffolding for the formation of a vascular system. In one aspect, the channels and periodic outlets are produced by a method comprising: drawing a fiber, wherein the fiber comprises i) a biodegradable cladding surrounding a hollow core having a diameter of about 100 microns to about 500 microns, and ii) at least one core of secondary biodegradable polymer having a diameter of about 10 microns to about 90 microns, wherein the at least one core of secondary biodegradable polymer is embedded within the biodegradable cladding. In some embodiments, the at least one core of secondary biodegradable polymer comprises polydioxone (PDO). In some embodiments, the biodegradable cladding comprises polylactic acid. In some embodiments, the method further comprises heating the drawn fiber to modify the at least one core of secondary biodegradable polymer into a plurality of independent units of the secondary biodegradable polymer as exemplified in FIG. 1D and FIG. 9 (part IV). In some embodiments, the plurality of independent units of the secondary biodegradable polymer is roughly spherical. In some embodiments, the method further comprises degrading the plurality of independent units to produce periodic outlets within the fiber. In some embodiments, the method further comprises degrading the biodegradable cladding. In some embodiments, the steps of degrading occur by introduction of cells and cell metabolism, by chemical means, or by thermal means.

In some embodiments, the cladding and core are comprise biodegradable materials. In some embodiments, the biodegradable materials may be selected from the group consisting of In some embodiments, the bioink may be composed of biodegrable synthetic polymers, such as poly(glycolicacid) (PGA), poly(lacticacid) (PLA), poly(lactide-co-glycolide), polyan-hydride, poly(propylenefumarate), polycaprolactone (PCL), polyethyleneglycol (PEG), polyurethane, or a combination thereof.

In some embodiments, the fiber is produced by drawing a fiber from a preform comprising i) a first core having an average diameter of about 100 microns to about 500 microns and ii) a second core having an average diameter of about 10 microns to about 70 microns to about 90 microns. In some embodiments, the method further comprises applying a focused heat to the drawn fiber, wherein the heat is capable of breaking up the second core into a plurality of periodic units having a roughly spherical shape. In some embodiments, the method comprises degrading the first core and plurality of period units. In some embodiments, the step of degrading is accomplished by cell metabolism, by thermal means, or by chemical means. For example, etching techniques may be used to sacrifice and remove the first and second core materials. After the step of degrading the core materials, a hollow void and periodic outlets remain. In some embodiments, the method further comprises coating the hollow void with a biocompatible material and coating the external surface of the fiber with a second biocompatible material. In some embodiments, the method further comprises contacting the fiber with a bioink to seed cells.

In some embodiments, the bioink is a gel matrix comprising cells. In some embodiments, the cells are selected from stem cells, liver cells, cancer cells, neurons, epithelial cells, endothelial cells, heart cells, or vascular cells. In some embodiments, the bioink comprises extracellular matrix (ECM). In some embodiments, the hollow void internal to the fiber is coated with a growth factor for example VEGF. In some embodiments, the outside of the fiber is coated with a growth factor such as PDGF. In this way, the cells are provided chemical and mechanosensory signals to form complex structures such as a vasculature system that is able to provide nutrients and oxygen exchange to a synthetic tissue or tissue construct. An exemplary embodiment, is provided in FIG. 2.

Figure 2:
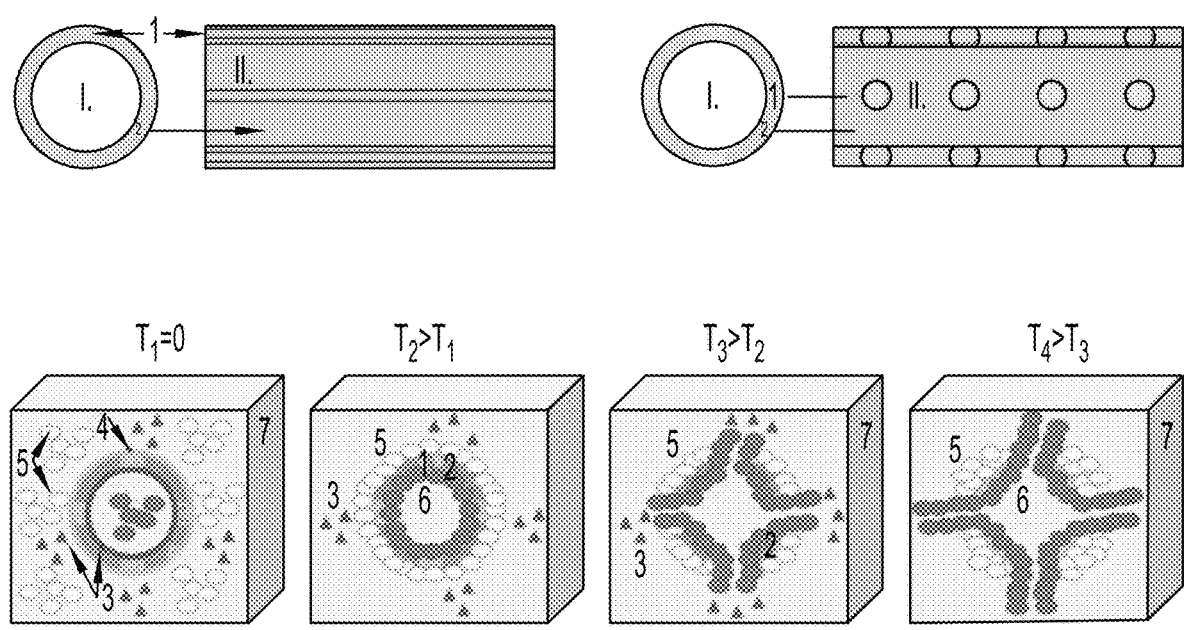
FIG. 2 is a diagram showing the formation of a fiber and its use to grow a vasculature.

Referring to FIG. 2, shows an exemplary embodiment of a vascularization fiber fabrication, schematics, and function: In part A shows a drawn fiber. I.—fiber cross section view, II.—fiber side view. 1—PDO cores embedded in a 2—PLA cladding of the hollow-core fiber; B. The fiber after the breakup of the PDO cores into an array of windows; C. Vascularization of bioprinted construct embedding the fiber. At the time $t_1=0$ the fiber, stream-coated from the inside with 3—VEGF and dip-coated on the outside with 4—PDGF, is embedded in 7—extracellular matrix bioink, containing tissue cells of interest (liver, cancer cells, neurons, or even stem cells, which later can be differentiated, depending on the application) bioink containing 5—SMC and 3—VEGF. EC in physiological solution are cyclically pumped through the center of a fiber. At the time $t_2>t_1$, the SMC and EC are driven towards the proangiogenic growth factors, PDGF and VEGF, respectively, forming the basic structure of the arteriole vessel of smooth muscle with internal endothelial lining, mediated at this time by the hydrolytically degradable fiber, embedding fibrin nanofibers. At the time $t_3>t_2$, the PDO windows, which have a faster degradation rate than the PLA cladding, are fully degraded, opening a path for EC to extend capillaries towards the VEGF in the bioink. At the time $t_4>t_3$, after the PLA cladding has dissolved, the final construct is ready. It consists of extracellular matrix bioink material hosting tissue cells of interest, and hierarchical blood vessel system consisting of realistic arterioles (SMC internally laid with EC, reinforced by fibrin nanofibers) with microcapillaries protruding the bioink throughout.

Figure 9:
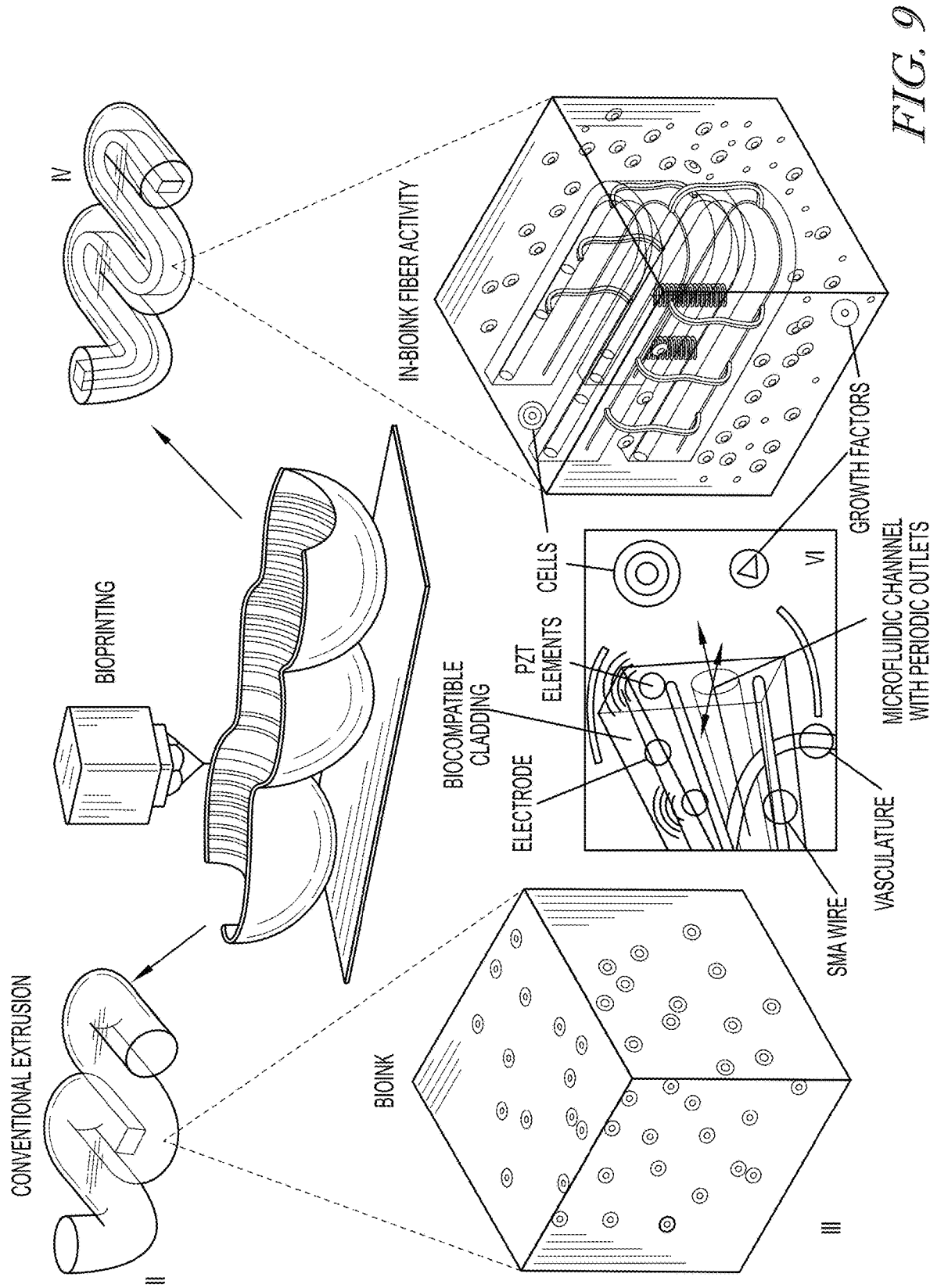
FIG. 9 illustrates another example of biointerfacing in accordance with this disclosure.

In another embodiment, channels and periodic outlets are produced in a method comprising drawing a fiber comprising cladding and two sacrificial cores, wherein the first core has a diameter of about 100 microns to about 250 microns and the second core has a diameter of about 10 microns to about 20 microns In some embodiments, the method further comprises breaking up the second core using heating techniques to produce discrete units of second core periodically spaced along the fiber as shown in FIG. 1D and FIG. 9 (part IV). In some embodiments, the method further requires removing the second core using a sequence of etching techniques to remove the second core material. In some embodiments, the cladding, the first core and the second core are formed from biocompatible materials, such as polycarbonate (PC) and cycloolefin copolymer (COC). In some embodiments, the fiber cladding comprises PC and the two cores comprise COC. In some embodiments, the method further comprises thinning the fiber down prior to removing the core materials. In some embodiments, the resulting fiber structure mimics an arteriorial network-sized channel with capillary-sized outlets. In some embodiments, a method of growing vascular tissue comprises contacting bioink surrounding the fiber with a chemical initiating vascular growth; supplying vascular cells through a central channel formed by the first core; and maintaining the vascular cells to grown into a capillary network that grows out of the micro outlets into a printed tissue.

Integration of Fibers into Complex Three-Dimensional Constructs

For a variety of applications, fibers produced as described above may be integrated or woven in complex three-dimensional constructs fabricated by additive manufacturing. In tissue, it is important to incorporate the fibers within the wall volume or at the wall internal surface of the model, depending on the fiber functionality. These fibers would be used for biostimuli and biosensing modalities, such as ultrasound imaging, shape tracking, peristaltic motion, bio-chemical delivery, surface morphology biomimetics (microvilli) and so forth, to create maturation support in terms of vascularization, innervation, muscular or peristaltic movement, connective tissue. The fibers may be smoothly integrated into three-dimensional prints of the gut, such as via the bioink gelma (gelatin methacryloyl) provided by CELLINK, a bioprinter manufacturer. In some examples, the fibers may be introduced into various realistic organ-dependent ex vivo tissue, such as skin or gut tissue. This may be done with or without incorporating cells such as GFP-reporter HEK 293 cells into the bioinks, though other types of cells may be used.

Printhead for Incorporating Fibers into a Print Feedstock

Figures 7A, 7B:
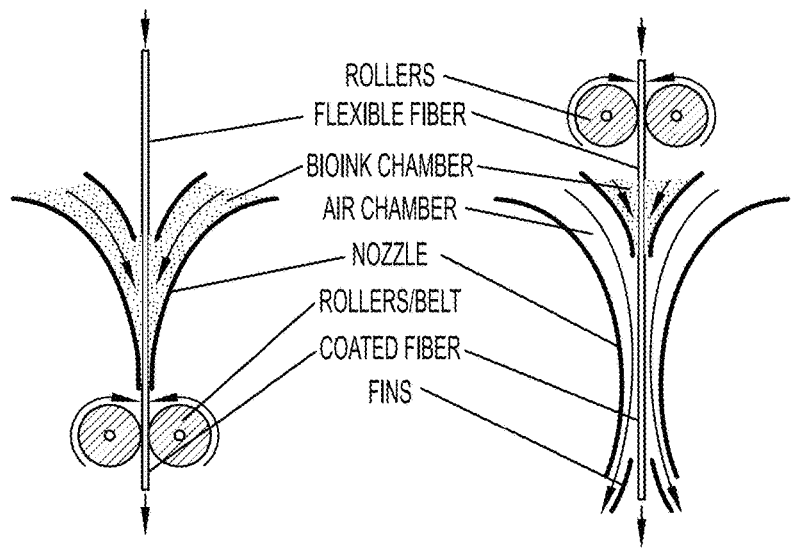
FIGS. 7A and 7B illustrate designs for printhead engineering.

In parallel, we are engineering a custom printhead that would enable an efficient incorporation of the fiber into the print feedstock. Here, the solutions grade by complexity that is correlated to the optimization of such integration. FIGS. 6A and 6B show a CAD design of the simplest printhead structure solution, in a standard Bio X printhead (FIG. 6A) has a spool mounted thereto (spool shown in FIG. 6B). An example bioprinting system is shown in FIG. 6C. FIGS. 7A and 7B show two more advanced designs for printhead engineering. These designs involve coating the fiber in bioink introduced at specific locations, using rollers and pneumatic feed. As shown in FIG. 7A, the fiber is dipped manually into the bioink at the beginning of its extrusion and spooled off by the shear stress applied by the surrounding bioink. The spool is set on a bearing allowing it to rotate with very low friction. The bioink is controlled by a hermetic sealing mechanism (not shown). As shown in FIG. 7B, the fiber is both pushed by rollers and dragged by pneumatic force through the bioink chamber onto the print platform. The bottom part of the pneumatic chamber has fins that guide the air flow away from the print platform. Other standard Bio X printheads can always be employed to deliver other specific biomaterials. All of this is done in a biosafety chamber of the printer. Therefore, the print-head add-ons are designed to resist the exposure to UV.

In terms of application, a platform with a specific arrangement of inlets and outlets can be fabricated using a variety of biocompatible thermoplastics using the Bio X (available from CELLINK) or biocompatible optical or autoclavable (reusable) resins using the Form 2 or Form 3 (available from Formlabs). This device can then be filled in a sterile environment using gel-based extracellular matrix and cells with the goal of creating artificial tissue. During both the platform and tissue printing, fibers can be weaved or integrated in the system, to remain as support structures or to biodegrade and become part of the tissue. Due to the nature of the computer-aided design models used in the printing of the platform, those can easily be used to simulate, dynamic, fluidic, thermal, and biological interactions, allowing for comparative expectations.

Biological Interfacing

Fiber technology is frequently utilized in various biomedical applications as chemical, biological, and physical sensors. Fiber-embedded sensors have been designed to monitor physical parameters such as stresses, temperature, pressure, and humidity or chemical parameters such as pH level, oxygen concentrations, and carbon dioxide concentrations. Fiber bundles are beneficial to embed multiple sensors together in a single system and in increasing signal reception levels, resulting in higher signal-to-noise ratios.

Lightness, flexibility, and unique optical properties are the main characteristics that lead the demand for fiber sensors in biomedical studies. To meet clinical usage requirements, preforms must be fabricated from biocompatible, non-toxic, and chemically inert materials to prevent immune reaction from the patient. Examples of smart fiber development include a neural fiber probe composed of a polymer and metal core composition that enables flexibility and bending stiffness of the neural probe as it provides in vivo optogenetic stimulation and delivers drugs as an input in order to record feedback electrical and physiological output signals. Another example is a fiber integrating microfluidic principles with complex crosssectional geometries and meter-long microchannels which analyzes cell separation by DEP. Live and dead cells are separated by inertial and dielectrophoretic forces by sheathless, high-throughput microfluidic cell separator which contains conductive materials in the microchannels.

The following strategies show a new array of possibilities where smart fibers are used in biological interfacing. In one embodiment, consider an artificial gut that can serve as a bioactive testing platform at the microscale and at the macroscale. With today's progress in tissue engineering, a variety of functionalities can be integrated in bioink coated fibers co-extruded using a bioprinter for tissue fabrication, as shown in FIG. 9 (I), which illustrates three-dimensional bioprinting of a tissue. FIGS. 9 (II) and 9 (III) illustrate the standard microextrusion of bioink and a conventional bioink with cells suspended in hydrogel. Traditionally, bio-printing research aims at creating tissue grafts for regenerative medical practice and does so by carefully designing the hydrogel (FIG. 9 (II)) with the appropriate nutrition and signaling molecules for the type of cells required based on the application (FIG. 9 (III)). Tissue engineering is very challenging to study as the whole biology of the system completely changes microseconds after the experiment has been launched. Monitoring and regularly tuning a tissue's maturation remains very complex.

This disclosure proposes a solution by introducing smart fibers in the design (FIG. 9 (IV)) to provide a better understanding of the climate and environmental growth. As discussed in embodiments above, the embedded fiber holds multiple functionalities (FIG. 9 (VI)) such as inducing vasculogenesis, ultrasonic imaging, peristaltic movement, and microfluidic flow. Control of the microenvironment takes place via the fiber hooked to syringe pumps and wired to an analytical software. The features of this application (FIG. 9 (V)), including pilot experimental data, are de-tailed in the next subsections.

A variety of functionalities are integrated in bioink coated fibers co-extruded using a bioprinter for tissue fabrication, as shown in FIG. 9 (I). Traditionally, bioprinting research aims at creating tissue grafts for regenerative medical practice and does so by carefully designing the hydrogel (FIG. 9 (II)) with the appropriate nutrition and signaling molecules for the type of cells required based on the application (FIG. 9 (III)). Tissue engineering is very challenging to study as the whole biology of the system completely changes microseconds after the experiment has been launched. Monitoring and regularly tuning a tissue's maturation remains very complex.

The current disclosure introduces smart fibers in the design (FIG. 9 (IV)) to provide a better understanding of the climate and environmental growth. The embedded fiber holds multiple functionalities (FIG. 9 (VI)) such as inducing vasculogenesis, ultrasonic imaging, peristaltic movement, and microfluidic flow. Control of the microenvironment takes place via the fiber hooked to syringe pumps and wired to an analytical software. The features of this application (FIG. 9 (V)) are detailed below.

The Extracellular Matrix and Vasculature

Tissue engineering is widely explored with the increase of artificial tissue needs, and the ability to bioprint realistic tissue has an important role to play in tomorrow's drug and treatment development. One of the biggest challenges is the design of the extracellular matrix (ECM), composed of proteins, growth factors, and other biomolecules, that guide the cell's contribution to the tissue. Naturally, the ECM gives purpose and structure to the cells, and its extraction typically works by de-cellularizing tissue and recycling or reusing the ECM for a new cellular construct. The ECM comes in the form of solvents, hydrogels, biopolymers, bioceramics, aerogels, or foams to provide biodegradable or resorbable structure to the tissue.

Due to tissue engineering's high complexity in defining the specifics of the biosystem—mechanical properties, scaffold dissolvability or absorption rates, initial cell types, nutrition, density and ratios, growth factors introduction, and its resulting bioactivity and tissue self-assembly—it is important to assess the behavior of different types of naturally produced ECM or artificially developed biomaterials in the presence of interacting cells. Moreover, viable tissue requires an organized vascular system that supplies nutrition and oxygen to the tissue for the health and growth of cells. Vascularization provides the natural microfluidic feed of biochemicals to initiate proliferation, specialization, interactions, and motion. The vascular network is formed by vasculogenesis, arteriogenesis, and angiogenesis. Vasculogenesis develops its network through the differentiation and division of endothelial stem cell. Angiogenesis forms new sprouts from existing vessels that are formed in the early embryonic vasculogenesis stage.

In-Fiber Microfluidic Feed

Microfluidic conduits with periodic microchannels for content delivery is used to weave microfluids to specific locations in tissue constructs. The liquefaction front at the boundary of the hot zone defines the droplets' pinch-off location as described previously. Multiple cores are therefore broken up in a spatially coherent manner. For example, a silica fiber including a platinum and a silicon core becomes a fiber tube with multiple outlets, by inducing the silicon core into an array of spheres and then thinning the fiber using hydrogen fluoride, etching the silicon spheres with potassium hydroxide and etching the platinum core with regal water. An example of the result is shown in FIG. 9 (V). The flexibility of fibers allows the microfluidic feed to be integrated in multiple ways in tissue construct. In FIG. 9 (IV), the microfluidic channels are used to provide the necessary cell type and growth factors to initiate vascularization and angiogenesis as the tissue reaches maturity.

Biomaterial and Biochemical Testing

Figure 8A:
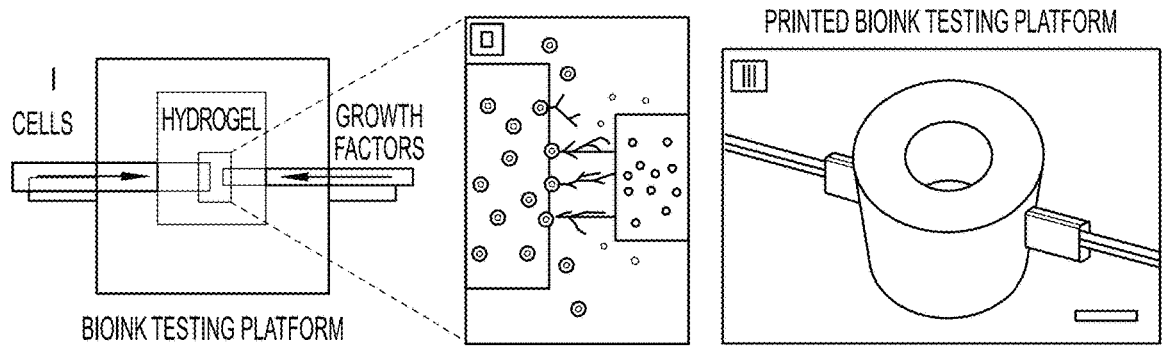
FIGS. 8A-8C illustrate pilot examples of biointerfacing in accordance with this disclosure.

In parallel to fiber development, a new testing platform (FIG. 8A (I)) was designed to analyze vascularization and cell-to-cell interactions in the presence of growth factors (FIG. 8A (II)). FIG. 8A (I) is a cross-section of the bioink testing platform showing fluidic feed. FIG. 8A (II) illustrates an example of the interaction of epithelial cells (blue circles on left) with vascular endothelial growth factors (yellow dots on right) in the platform, resulting in vasculogenesis excreted by the cells (red lines in the center). The platforms were printed in high resolution at an orientation of 30 from biocompatible resin by stereolithography (Formlabs' Form 2 and Dental LT Clear resin). The print result, printed in biocompatible resin and shown in FIG. 8A (III) (scale bar=5 mm), was assembled with two glass capillary tubes with outer diameters of 1.8 mm and 1.0 mm where biological agents are fed. Initial trials assess diffusion parameters of biochemicals and the growth of cellular colonies in various biocompatible materials. These platforms are designed to be single-use. In 2 hours, 24 testing wells are printed at a relatively low cost. The distance between each capillary outlet of two parallel fibers is adjusted between 100 m and 400 m to investigate the optimum vasculogenesis range that is accepted around 200 meters (m). In one embodiment, the medium of interaction in the well's chamber hosts commercial bioinks (Cellink, USA). In one embodiment, it contains sodium alginate and nanofibrillar cellulose. In one embodiment, it contains gelatin methacryloyl. In another embodiment, in-house biomaterials are used. The glass capillary tubes shown in FIG. 8A (III) may be replaced by the microfluidic fibers shown in FIG. 9 (IV) and FIG. 9 (V).

Peristaltic Motion

Shape memory alloy (SMA) wires are lightweight, non-corrosive, and cost-efficient actuating materials for refined applications in a variety of applications such as prosthetic biomimicry, self-expandable surgical implants, and aerospace engineering. SMAs are metal compounds known for their shape memory effect and pseudoelasticity. Although such properties are typically found in nickel-titanium, these properties can be found in a range of different other metal alloys. FIG. 10(c) shows the shape memory effect in terms of temperature, stress, and strain. As shown, at low temperatures, the SMA in its martensite solid state is deformed by mechanical force, and when thermally induced, goes through a non-diffusive molecular reordering, converting to an austenite solid state. When cooled, the material will return to its initial martensite form, hence the shape memory effect. This thermal cycle is defined by four temperatures, the starting and finishing martensite and austenite temperatures ($M_s$, $M_f$, $A_s$, and $A_f$), which specifies the start and end of transition periods between states. When the SMA is deformed in as martensite, the molecular de-ordering is defined as detwinning, and it allows the material to experience elongation, which is particularly useful for actuation applications. Essentially, the shape memory effect cycle can occur hundreds of times for an average elongation of 6% and contraction, hence its nickname "muscle wire" for its close similarity to muscular myofibrils.

This unique characteristic was first reported in 1938 and can also be triggered by magnetic field energy, namely FMSA, and can be found in polymers (SMP) as well. Today, SMA's mechanical fatigue and fracture, elasticity, and thermodynamics have been characterized well experimentally and mathematically, and its behavior has been modeled Although the shape memory effect allows for nice contraction behavior of a material, for appropriate robotic applications, the motion needs to be reversible. Typically, an SMA is set in tandem with an opposite mechanism, such as springs, electric drives, elastic bands, or simply another SMA wire. Furthermore, the assembly changes whether it is a linear or rotatory actuation and if the opposing contractions of the actuation are equal. Although wires are thin and weak alone, they can be bundled together to reach the desired force and keep its shape memory effect response time. SMA wires can also be coiled around a capstan to provide greater elongation over shorter distances. Various strategies have been reviewed and chosen for specific applications. The thermal induction is typically best controlled by powering the SMA wire and varying the input current of the order of hundreds of milliamperes. Cooling can be done naturally or by including heat sinks and ventilation.

Figure 8B:
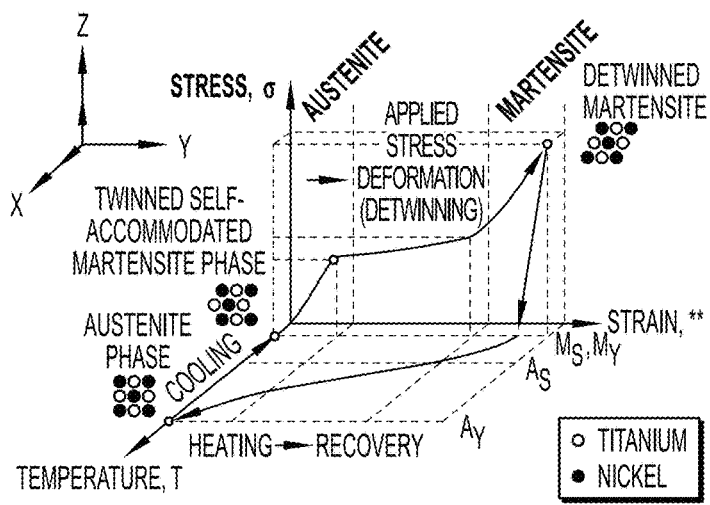
Figure 8C:
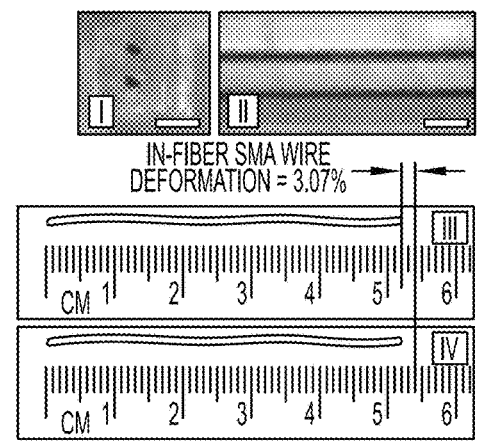

Fiber drawing technology allows for the manipulation of different material characteristics and to provide to an SMA wire an elastic coating that helps preserve the disorder state of the SMA fiber. As shown in FIGS. 8C (I) and 8C (II), a fiber can be drawn with multiple embedded SMA wires. Styrene-ethylene-butylene-styrene (SEBS) was chosen as the surrounding structure to the SMA wires. SEBS is a copolymer elastomer that can withstand the drawing temperature of 80° C. FIG. 8B illustrates the phases of the nickel-titanium material of the SMA wires during heating and cooling under varying stress and strain.

Though actuation works with lower efficiency than bare SMA wires, the back-and-forth motion through heating (FIG. 8C (III)) and cooling (FIG. 8C (IV)) cycles is observed for a deformation of approximately 3.07%. The wires were physically pulled and heated using a hot plate to prove the concept. Heating by current would allow speeding up the shape memory effect and controlling better the heat's diffusion through the fiber. The 5.35-mm wire was measured to have a diameter of 0.11 mm and a resistance of 18.2 was recorded across the fiber segment. To provide a frame of reference, according to SMA wire manufacturers (Dynalloy, Inc.), a 0.1-mm-thick wire made of nickel and titanium requires approximately 200 mA of current for a 1 s contraction.

Controlling each wire individually would allow for directional movement, and adding more SMA wires to the design would allow multi-directional motion and greater contraction strength. Moreover, if FMSA wires were used, the control of the motion could become locally controllable via tuning of the interacting magnetic field. Additionally, the FAMES Lab's drawing tower having the ability to rotate a preform as it is drawing into a fiber enables the possibility to manufacture spring-like structures of SMA wires in the fiber which allows for greater deformation, similar to commercially available SMA springs. Clearly, varieties of strategies are enabled with in-fiber SMA wires.

Biosensing

Biosensors are developed in a wide variety of ways. They can be designed label-based or label-free to detect specific expressions from biological elements such as cells, bacteria, hormones, proteins, DNA, and more, from sampling blood, urine, saliva, sweat, or tears. Psychophysiological conditions can be observed from real-time biofeedback such as blood pressure, electrodermal activity, skin conductance, respiration and heart rates, and more. Bioimaging has been done by optical imaging, ultrasound, magnetic resonance frequency, computed tomography, near-infrared spectroscopy, quantum dot probing, and by many more techniques.

In optical fiber research, previous biosensing fibers have been fabricated relying on silicon photonic crystal detection of biological radiation. Photonic crystal technology has been used before to monitor in label-free real-time cellular morphology and survival. Such progress in biophotonics has led to hollow-core microstructured fibers visible under MRI. The hollow core allows the propagation of the optical radiations along the fiber over very long distances. The geometry of the hollow fibers varies to tune the photonic bandgaps and dispersion of different detected wavelengths. The inner walls of these hollow tubes are coated with oppositely charged polyelectrolytes and magnetite nanoparticles which are used as contrast agents for MRI. Such design therefore enables new biomedical precision diagnosis opportunities, for example, in the observations of neural activity in vivo.

Ultrasonography technology enables us to observe density of cells in liquid or gel in a non-intrusive manner. Ultrasonic probes typically function according to the piezoelectric effect (generation of electricity from applied stress), which was first discovered by Jacques and Pierre Curie in 1880. The inverse piezoelectric effect (deformation of a piezoelectric crystal from an applied electric field) was induced mathematically in 1881 and later developed into ultrasonic submarine detection for World War I military applications. Thereon, sonar applications have been diverse, such as underwater imaging and fish-finding and energy harvesting.

The piezoelectric elements convert electrical energy to and from mechanical energy and transmit sound waves between each other. All frequency and bandwidth parameters require precise regulation, and good energy transmission requires good acoustic and damping matching impedances. Two fibers with integrated piezoelectric elements, designed as pulsing emitter and receiver, can create an ultrasonic waveguide between each other to measure density over the wave's trajectory. This fiber enables us to sense the microstructures of the environment as the tissue reaches maturation.

The piezoelectric elements are created by capillary breakup from a PZT core for example. PZT elements have an acoustic impedance of $33.7 \times 10^6$ kg/m$^2$s with a resonance frequency below 25 MHz. The produced spheres are lined with conductive electrodes to a transducer. This setup provides the feedback in a control system to better adjust microfluidic and motion feed. The in-fiber ultrasonic imaging of the microenvironment clearly helps understand how the tissue environment behaves over time. Thus, the concept of VLSI-fi may enable fabrication of active biomimetic scaffolds for engineered tissues with realistic microstructures.

In some embodiments, temperature sensors may be incorporated into the fiber. In one aspect, a method of producing a temperature sensor comprises drawing a fiber comprising i) polycarbonate, ii) a core comprising selenium-sulfur semiconducting material, and iii) two copper electrodes on either side of the selenium-sulfur core, heating the fiber to break up the selenium-sulfur semiconducting core into individual units having a spherical shape. In some embodiments, the step of breaking up the semiconductor core occurs by providing a directed heat source at the fiber to liquefy the semiconductor core forming a plurality of individual semiconducting units. In some embodiments, during the process of breaking up the selenium-sulfur core into a plurality of separate units, each unit makes contact with the two copper electrodes. For example, the selenium-sulfur core material when broken up into a plurality of individual units, becomes wider in a smaller length of space making it possible to make contact between the two copper electrodes on either side.

The temperature sensor may be referred to as a thermistor and is configured to deliver data related to temperature changes. For example, a fiber comprising a temperature sensor may be contacted with a voltage running through the copper wires, and the resultant current will change when the semiconductor core changes in response to a temperature change.

In some embodiments, a method is provided for determining the effects of a pharmaceutical composition on a plurality of living cells using a 3D printed platform. In some embodiments, the method comprises providing the 3D printed platform, the 3D printed platform including (i) a container 3D printed from a biocompatible resin and defining a reaction chamber, (ii) a quantity of bioink including the plurality of living cells received within the reaction chamber, (iii) at least one microstructured fiber extending through the container from the exterior of the container to the reaction chamber and into the bioink. In some embodiments, the method further comprises introducing the pharmaceutical composition into the bioink comprising a plurality of living cells via the at least one microstructured fiber. In some embodiments, the method further comprises determining the effects of the pharmaceutical composition on the plurality of living cells. In some embodiments, a pharmaceutical assay may include testing the effects of antibiotic mixtures of narrow or broad spectrum, immune cell response to poisoning by plurality of heavy metals, or testing nanotoxicity of materials nominally biocompatible when in bulk.

In some embodiments, the fiber may be used in a method for chemical detection. In some embodiments, the method comprises a drawn fiber comprising a chemical sensor. In some embodiments, the chemical sensor comprises a transduction element exposed to the environment to sense a chemical species of interest. In some embodiments, transduction elements may be positioned directly within one or more periodic outlets. In some embodiments, transduction elements may be embedded in a wall of the fiber, e.g., arranged in the fiber cladding, or other suitable geometry, for example, coating a bundle of thinner fibers or threads that are disposed in a hollow microcapillary of the fiber. In some embodiments, the transduction element comprises chemiluminescent sensing material capable of producing an optical signal when the transduction element interacts with a specified chemical species. Alternatively, the transduction element may comprise a fluorescent material having a quiescent level of fluorescence that is quenched upon interaction with an intake species.

Additional embodiments are also contemplated:

Clause 1. A method of producing bioengineered tissue, the method comprising: coating a microstructured fiber with a bioink comprising a plurality of living cells, wherein the microstructured fiber is embedded with a number of microfluidic channels defining periodic outlet apertures, applying the coated microstructured fiber to an anatomic model of an organ, and allowing the bioengineered tissue to mature into functional tissue.

Clause 2. The method of clause 1, wherein the microfluidic channels and outlet apertures of the microstructured fiber are configured to function as an artificial blood-vessel system to the bioengineered tissue, the artificial blood-vessel system supplying building material for the proliferation of the plurality of living cells.

Clause 3. The method of clause 1, wherein: the microstructured fiber is further embedded with a number of ultrasonic transducers.

Clause 4. The method of clause 1, wherein: the microstructured fiber is further embedded with a number of sensors.

Clause 5. The method of clause 4, wherein: the sensors include chemical sensors.

Clause 6. The method of clause 4, wherein: the sensors include temperature sensors.

Clause 7. The method of clause 1, wherein the microstructured fiber is further embedded with a number of ultrasonic transducers, a number of chemical sensors, and a number of temperature sensors and provides peripheral innervation of the bioengineered tissue, thereby enabling imaging of proliferation or death of the plurality of living cells and monitoring of metabolic processes of the bioengineered tissue.

Clause 8. A method of producing bioengineered tissue, the method comprising: coating a microstructured fiber with a bioink comprising a plurality of living cells, applying the coated microstructured fiber to an anatomic model of an organ, and allowing the bioengineered tissue to mature into functional tissue.

Clause 9. A method of bioprinting a plurality of the microstructured fiber of claim 1, the method comprising: printing a plurality of fiber preforms; drawing the plurality of fiber preforms into a plurality of fibers; axially patterning the plurality of fibers by means of material selective spatially coherent capillary instability to assemble the plurality of microstructured fibers into an array in which at least two discrete fibers of the plurality of the microstructured fibers are contacted in parallel.

Clause 10. The method of clause 9, wherein the plurality of preforms are polycarbonate.

Clause 11. The method of clause 9, wherein the plurality of preforms include at least one fiber selected from the group comprising COC, PSU, PC, ECOC, SEBS, PDMS, PVDF, PEI, or PMMA.

Clause 12. The method of clause 9, wherein the plurality of preforms are multimaterial.

Clause 13. The method of clause 9, wherein the axial patterning of the plurality of fibers is spatially coherent.

Clause 14. The method of clause 9, wherein the axial patterning of the plurality of fibers is at least partially achieved by capillary break-up.

Clause 15. A method of producing bioengineered tissue, the method comprising: coating a fiber with a bioink comprising a plurality of living cells, wherein the fiber is embedded with a plurality of integrated devices (i.e., devices coupled through electronic links, such as common electrical contacts, or photonic links, such as fiber-embedded optical cores).

Clause 16. The method of clause 15, wherein the integrated devices are microfluidic channels.

Clause 17. The method of clause 16, wherein the microfluidic channels have outlet apertures.

Clause 18. The method of clause 17, wherein the outlet apertures are periodic.

Clause 19. The method of clause 15, wherein the integrated devices are ultrasonic transducers.

Clause 20. The method of clause 15, wherein the integrated devices are sensors.

Clause 21. The method of clause 20, wherein the sensor is a chemical sensor.

Clause 22. The method of clause 20, wherein the sensor is a temperature sensor.

Clause 23. A bioengineered tissue comprising: a plurality of fibers drawn from a plurality of fiber preforms, wherein the fibers are coated with bioink comprising a plurality of living cells and embedded with a plurality of integrated devices.

Clause 24. The bioengineered tissue of clause 23, wherein the integrated device is a microfluidic channel.

Clause 25. The bioengineered tissue of clause 24, wherein the microfluidic channel has outlet apertures.

Clause 26. The bioengineered tissue of clause 25, wherein the outlet apertures are periodic.

Clause 27. The bioengineered tissue of clause 23, wherein the integrated device is an ultrasonic transducer.

Clause 28. The bioengineered tissue of clause 23, wherein the integrated device is a sensor.

Clause 29. The bioengineered tissue of clause 28, wherein the sensor is a chemical sensor.

Clause 30. The bioengineered tissue of clause 28, wherein the sensor is a temperature sensor.

Clause 31. A method for determining the effects of a pharmaceutical composition on a plurality of living cells using a 3D printed platform, the method comprising: providing the 3D printed platform, the 3D printed platform including (i) a container 3D printed from a biocompatible resin and defining a reaction chamber, (ii) a quantity of bioink including the plurality of living cells received within the reaction chamber, (iii) at least one microstructured fiber extending through the container from the exterior of the container to the reaction chamber and into the bioink; introducing the pharmaceutical composition into the bioink comprising a plurality of living cells via the at least one microstructured fiber; and determining the effects of the pharmaceutical composition on the plurality of living cells.

Clause 32. A method for studying a disease state of a plurality of living cells using a 3D printed platform, the method comprising: providing the 3D printed platform, the 3D printed platform including (i) a container 3D printed from a biocompatible resin and defining a reaction chamber, (ii) a quantity of bioink including the plurality of living cells received within the reaction chamber, (iii) at least one microstructured fiber extending through the container from the exterior of the container to the reaction chamber and into the bioink; introducing conditions that alter the health of the plurality of cells; and determining the effects of the altered health on the plurality of living cells.

Clause 33. A method of producing bioengineered tissue, the method comprising: coating a microstructured fiber with a bioink comprising a plurality of living cells, wherein the microstructured fiber is an ultrasonic imaging fiber, a muscular actuation fiber, an antiseptic fiber; and applying the coated microstructured fiber to an anatomic model of an organ, and allowing the bioengineered tissue to mature into functional tissue.

Clause 34. A method of producing bioengineered tissue, the method comprising: coating a microstructured fiber with a bioink comprising a plurality of living cells, applying the coated microstructured fiber to an anatomic model of an organ, allowing the bioengineered tissue to mature into functional tissue, and functionally coupling a biological supporting system to the tissue.

Clause 35. The method of clause 34, wherein the biological support system includes at least one of the following a muscular actuation fiber, a peristaltic actuation fiber.

Clause 36. A bioengineered tissue comprising: a plurality of fibers drawn from a plurality of fiber preforms, wherein the fibers are coated with bioink comprising a plurality of living cells and embedded with a plurality of integrated devices; and a biological supporting system functionally coupled to the tissue.

Clause 37. The tissue of clause 36, wherein the biological support system includes at least one of the following a muscular actuation fiber, a peristaltic actuation fiber.

Based upon the foregoing disclosure, it should now be apparent that the systems and methods for engineering tissues and organs described above will carry out the objects set forth hereinabove. Namely, these systems and methods are capable of providing a tissue scaffold for the growing bioengineered tissue, enabling monitoring of local tissue conditions in the growing bioengineered tissue in real time, and enabling manipulation of local conditions within the growing bioengineered tissue to help ensure that the maturing engineered tissue develops and maintains the correct cell types, viability, and appropriate extracellular structures. It is, therefore, to be understood that any variations evident fall within the scope of the present disclosure and thus, the selection of specific component elements can be determined without departing from the spirit of the invention herein disclosed and described.

What is claimed is:

1. A bioengineered system comprising:
   i) a bioink and
   ii) a fiber extending through the bioink along a first axis, the fiber comprising a hollow core and a cladding having an outer surface and surrounding the hollow core,
   wherein the cladding is formed to include an outlet that extends from the outer surface to the hollow core so that the hollow core and the bioink are in fluid communication.

2. The bioengineered system of claim 1, wherein the hollow core has a diameter that is perpendicular to the first axis of about 100 microns to about 300 microns.

3. The bioengineered system of claim 1, wherein the outlet has a diameter of about 5 microns to about 25 microns.

4. The bioengineered system of claim 1, wherein the hollow core and the outlet each comprise a core coating.

5. The bioengineered system of claim 4, wherein the core coating comprises a first growth factor.

6. The bioengineered system of claim 1, wherein the outer surface of the cladding is coated with an outer coating.

7. The bioengineered system of claim 6, wherein the outer coating comprises a second growth factor.

8. The bioengineered system of claim 1, wherein the bioink comprises an extracellular matrix and cells distributed throughout the extracellular matrix.

9. The bioengineered system of claim 8, wherein the cells comprise stem cells.

10. The bioengineered system of claim 1, wherein the cladding comprises a biocompatible material.

11. The bioengineered system of claim 10, wherein the biocompatible material is biodegradable.

12. The bioengineered system of claim 1, further comprises a sensing fiber, the sensing fiber including:
    i) a first metallic core and a second metallic core extending along the axis;
    ii) a segmented device located between the first metallic core and the second metallic core, and
    iii) a cladding surrounding the first metallic core, the second metallic core, and the segmented device, wherein the cladding comprises a material selected from the group consisting of COC, PSU, PC, ECOC, SEBS, PDMS, PVDF, PEI, and PMMA.

13. The bioengineered system of claim 12, wherein the segmented device comprises a first spherical component and a second spherical component, and wherein the first spherical component contacts the first metallic core and the second spherical component, and the second spherical component contacts the first spherical component and the second metallic core.

14. The bioengineered system of claim 13, wherein the segmented device extends along a second axis about perpendicular to the first axis.

15. The bioengineered system of claim 14, wherein the segmented device is a piezoelectric device.

16. The bioengineered system of claim 14, wherein the segmented device detects chemicals.

17. The bioengineered system of claim 14, wherein the segmented device measures a temperature.

18. The bioengineered system of claim 12, wherein the fiber and the sensing fiber are coupled together.

19. The bioengineered system of claim 1, comprising a syringe pump coupled the fiber.

20. A method of producing a biological support system comprising:
    bioprinting a bioink and
    a fiber extending through the bioink along an axis, the fiber comprising a hollow core and a cladding having an outer surface and surrounding the hollow core,
    wherein the cladding is formed to include an outlet that extends from the outer surface to the hollow core so that the hollow core and the bioink are in fluid communication.

* * * * *